(12) United States Patent
Anand et al.

(10) Patent No.: US 10,653,442 B2
(45) Date of Patent: May 19, 2020

(54) DRUG DELIVERY SYSTEMS AND METHODS

(71) Applicant: Alcyone Lifesciences, Inc., Lowell, MA (US)

(72) Inventors: PJ Anand, Lowell, MA (US); Morgan Brophy, Boston, MA (US); Deep Arjun Singh, Cambridge, MA (US); Greg Eberl, Acton, MA (US); Ayesha Arzumand, North Billerica, MA (US); Stela Moura, Lowell, MA (US)

(73) Assignee: ALCYONE LIFESCIENCES, INC., Lowell, MA (US)

( * ) Notice: Subject to any disclaimer, the term of this patent is extended or adjusted under 35 U.S.C. 154(b) by 218 days.

(21) Appl. No.: 15/849,705

(22) Filed: Dec. 21, 2017

(65) Prior Publication Data

US 2018/0185058 A1    Jul. 5, 2018

Related U.S. Application Data

(60) Provisional application No. 62/437,168, filed on Dec. 21, 2016.

(51) Int. Cl.
*A61B 17/34* (2006.01)
*A61M 5/172* (2006.01)
(Continued)

(52) U.S. Cl.
CPC ........ *A61B 17/3401* (2013.01); *A61B 5/0205* (2013.01); *A61B 5/032* (2013.01);
(Continued)

(58) Field of Classification Search
CPC .......... A61M 5/14276; A61M 25/0084; A61M 25/0068; A61M 25/10; A61M 25/1011;
(Continued)

(56) References Cited

U.S. PATENT DOCUMENTS 5,254,089 A * 10/1993 Wang .................... A61M 25/10
604/103.02
5,325,865 A      7/1994 Beckman et al.
(Continued)

OTHER PUBLICATIONS

Alperin, N. et al., "Magnetic resonance imaging-based measurements of cerebrospinal fluid and blood flow as indicators of intracranial compliance in patients with Chiari malformation," J. Neurosurg., 2005, v. 103, pp. 46-52.
(Continued)

*Primary Examiner* — Manuel A Mendez
(74) *Attorney, Agent, or Firm* — Marshall, Gerstein & Borun LLP

(57) ABSTRACT

Drug delivery systems and methods are disclosed herein. In some embodiments, a drug delivery system can be configured to deliver a drug to a patient in coordination with a physiological parameter of the patient (e.g., the patient's natural cerebrospinal fluid (CSF) pulsation or the patient's heart or respiration rate). In some embodiments, a drug delivery system can be configured to use a combination of infusion and aspiration to control delivery of a drug to a patient. Catheters, controllers, and other components for use in the above systems are also disclosed, as are various methods of using such systems.

19 Claims, 22 Drawing Sheets

(51) Int. Cl.
*A61B 5/03* (2006.01)
*A61B 5/00* (2006.01)
*A61B 5/0205* (2006.01)
*A61M 25/00* (2006.01)
*A61M 25/09* (2006.01)
*A61M 25/01* (2006.01)
*A61M 27/00* (2006.01)
*A61M 25/06* (2006.01)

(52) U.S. Cl.
CPC ......... *A61B 5/4839* (2013.01); *A61M 5/1723* (2013.01); *A61M 25/0026* (2013.01); *A61M 25/0041* (2013.01); *A61M 25/0068* (2013.01); *A61M 25/0082* (2013.01); *A61M 25/0097* (2013.01); *A61M 25/0147* (2013.01); *A61M 27/006* (2013.01); *A61M 2005/1726* (2013.01); *A61M 2025/0002* (2013.01); *A61M 2025/0003* (2013.01); *A61M 2025/0007* (2013.01); *A61M 2025/0031* (2013.01); *A61M 2025/0057* (2013.01); *A61M 2025/0681* (2013.01); *A61M 2025/09141* (2013.01); *A61M 2025/09175* (2013.01); *A61M 2202/0464* (2013.01); *A61M 2210/1003* (2013.01); *A61M 2230/005* (2013.01)

(58) Field of Classification Search
CPC ................ A61M 27/006; A61M 25/00; A61M 25/0147; A61M 25/0074; A61B 17/32037; A61B 17/22; A61B 17/3478; A61B 18/1492; A61F 7/12
See application file for complete search history.

(56) References Cited

U.S. PATENT DOCUMENTS

| | | | |
|---|---|---|---|
| 5,352,683 A | 10/1994 | Mayer et al. | |
| 5,502,058 A | 3/1996 | Mayer et al. | |
| 5,814,014 A | 9/1998 | Elsberry et al. | |
| 7,014,624 B2 | 3/2006 | Meythaler et al. | |
| 7,226,430 B2 | 6/2007 | Ludin | |
| 9,682,193 B2 | 6/2017 | Anand et al. | |
| 2003/0014016 A1 | 1/2003 | Purdy | |
| 2004/0024358 A1 | 2/2004 | Meythaler et al. | |
| 2004/0037986 A1* | 2/2004 | Houston | A61F 2/06 428/36.9 |
| 2004/0193045 A1 | 9/2004 | Scarborough et al. | |
| 2004/0254525 A1 | 12/2004 | Uber et al. | |
| 2005/0020962 A1 | 1/2005 | Reich et al. | |
| 2005/0075624 A1 | 4/2005 | Miesel | |
| 2005/0148927 A1 | 7/2005 | Ludin | |
| 2006/0135945 A1 | 6/2006 | Bankiewicz et al. | |
| 2006/0199779 A1 | 9/2006 | Goregaoker et al. | |
| 2007/0142770 A1* | 6/2007 | Rioux | A61M 37/00 604/93.01 |
| 2009/0054824 A1 | 2/2009 | Melsheimer et al. | |
| 2010/0312084 A1 | 12/2010 | Radojicic | |
| 2011/0288408 A1 | 11/2011 | Chinchoy | |
| 2012/0130314 A1* | 5/2012 | Stonebridge | A61M 1/3655 604/175 |
| 2012/0330249 A1* | 12/2012 | Clark | A61M 25/007 604/264 |
| 2013/0035660 A1 | 2/2013 | Anand | |
| 2014/0012226 A1 | 1/2014 | Hochman | |
| 2016/0331897 A1 | 11/2016 | Anand et al. | |
| 2017/0258996 A1 | 9/2017 | Anand et al. | |

OTHER PUBLICATIONS

Hettiarachchi, H. D. M., et al., "The Effect of Pulsatile Flow on Intrathecal Drug Delivery in the Spinal Canal," Annals of Biomed. Eng., 2011, v. 39, pp. 2592-2602.
Invitation to Pay Additional Fees for Application No. PCT/US16/31719, dated Jul. 12, 2016 (2 pages).
International Search Report and Written Opinion for Application No. PCT/US16/31719, dated Sep. 26, 2016 (15 pages).
International Search Report and Written Opinion for Application No. PCT/US2017/067796 (10 pages).
Seo, E., et al., "Computed tomographic evaluation of cervical vertebral canal and spinal cord morphometry in normal dogs," J. Vet. Sci., 2014, v. 15, pp. 187-193.
U.S. Appl. No. 15/151,585, filed May 11, 2016, Drug Delivery Systems and Methods.
U.S. Appl. No. 15/605,449, filed May 25, 2017, Drug Delivery Systems and Methods.

* cited by examiner

FIG. 19

DRUG DELIVERY SYSTEMS AND METHODS

CROSS-REFERENCE TO RELATED APPLICATIONS

This application claims priority to U.S. Provisional Application No. 62/437,168 filed on Dec. 21, 2016, which is hereby incorporated by reference in its entirety.

FIELD

Systems and methods are disclosed herein for delivering a drug to a subject (e.g., via intrathecal delivery into the cerebrospinal fluid (CSF) or subarachnoid space of the subject's brain or spine).

BACKGROUND

There are many instances in which it may be desirable to deliver a drug to a patient. The term "drug" as used herein refers to any functional agent that can be delivered to a human or animal subject, including hormones, stem cells, gene therapies, chemicals, compounds, small and large molecules, dyes, antibodies, viruses, therapeutic agents, etc.

Delivery of the drug can be done in a systemic manner, or can be targeted to a particular location or a particular distribution pattern. Targeted drug delivery can be challenging, however, as there are many instances in which the intended delivery target is not accessible, or not accessible in a minimally-invasive manner.

The natural physiology of the patient can also present drug delivery challenges. For example, achieving a desired or optimal drug distribution via intrathecal delivery can be difficult, at least in part due to the natural flow of CSF within the patient, which tends to be oscillatory and pulsatile with little net flow. Traditional techniques which involve delivering a large quantity of a drug to the intrathecal space and relying on natural diffusion to distribute the drug are inefficient and may be harmful to the patient.

There is a continual need for improved drug delivery systems and methods.

SUMMARY

Drug delivery systems and methods are disclosed herein. In some embodiments, a drug delivery system can be configured to deliver a drug to a patient in coordination with a physiological parameter of the patient (e.g., the patient's natural cerebrospinal fluid (CSF) pulsation or the patient's heart or respiration rate). In some embodiments, a drug delivery system can be configured to use a combination of infusion and aspiration to control delivery of a drug to a patient. Catheters, controllers, and other components for use in the above systems are also disclosed, as are various methods of using such systems.

In some embodiments, a drug delivery device can include an elongate body having a fluid lumen formed therein; and a fluid port formed in the delivery device, the fluid port being defined by a helical slit formed in a wall of the delivery device.

The helical slit can extend from an interior surface of the body to an exterior surface of the body. The helical slit can act as a fluid communication path between an interior of the fluid lumen and an exterior of the delivery device. The helical slit can be formed through an exterior wall of the delivery device. The helical slit can be formed in a sidewall of a reduced-diameter portion of the delivery device. The helical slit can be formed in a sidewall of an inner tube that projects from a distal end of the body. The delivery device can include an atraumatic distal tip defined by a substantially spherical bulb. The delivery device can include a second, distal-facing fluid port. The delivery device can include a tapered transition between a larger diameter proximal portion of the delivery device and a reduced diameter distal portion of the delivery device. The tapered transition can be at least one of conical, convex, and concave. The delivery device can be or can include a catheter. The delivery device can be or can include a needle. The delivery device can include an inflatable member disposed at a distal end of the delivery device. The inflatable member can be deployable from within a sharpened distal tip of the device. The inflatable member can include a fluid port therein. The fluid port of the inflatable member can include a helical slit.

In some embodiments, a drug delivery device can include an elongate body having a fluid lumen therein and a fluid port through which fluid can move between an interior of the fluid lumen and a location exterior to the delivery device; wherein at least a portion of the fluid lumen is helically-shaped.

The helically-shaped portion of the fluid lumen can be adjacent to the fluid port. The helically-shaped portion of the fluid lumen can include a tubular passage that defines a plurality of looped coils.

In some embodiments, a drug delivery device can include a needle having a sharpened distal tip; and an inflatable member selectively deployable from a distal end of the sharpened tip, the inflatable member having a fluid port formed therein; wherein the fluid port comprises a helical slit.

In some embodiments, a patient-specific infusion method can include determining a total CSF volume of a patient; aspirating a volume of CSF from the patient based on the determined total CSF volume of the patient; and infusing a drug into an intrathecal space of the patient.

The method can include, after infusing the drug, infusing the aspirated CSF of the patient to push the drug in a desired direction within the intrathecal space. The total CSF volume can be determined from a pre-operative image of the patient's central nervous system. The aspirated volume of CSF can be in the range of about 1% to about 20% of the total CSF volume of the patient. The drug can be infused while the volume of CSF is aspirated.

In some embodiments, a drug delivery method can include inserting a needle into an intrathecal space of a patient; inserting a fluid delivery catheter through the needle and into the intrathecal space; infusing a drug through the catheter and into the intrathecal space; and infusing a chaser through the needle behind the drug to push the drug through the intrathecal space.

The chaser can include at least one of a drug, a buffer, artificial CSF, natural CSF previously aspirated from the patient, and saline. The chaser can include previously-aspirated CSF. The CSF can be aspirated and infused using the same syringe in a closed system. The needle can protrude into the intrathecal space by a distance in the range of 0 cm to 1 cm. The catheter can protrude from the needle by a distance in the range of 0 cm to 1 cm.

In some embodiments, a drug delivery system includes a catheter having at least one fluid lumen; a pump configured to infuse fluid through the catheter; a sensor configured to measure a physiological parameter of a patient; and a controller that controls the pump to coordinate infusion of a drug through the catheter with the physiological parameter measured by the sensor.

The controller can synchronize infusion frequency with a frequency of a patient's natural intrathecal pulsation as measured by the sensor. The controller can synchronize infusion phase with a phase of a patient's natural intrathecal pulsation as measured by the sensor. The controller can establish a sinusoidal approximation of the patient's natural intrathecal pulsation as measured by the sensor. The controller can synchronize infusions with the ascending wave of the sinusoidal approximation. The controller can synchronize infusions with the descending wave of the sinusoidal approximation. The sensor can be configured to measure intrathecal pressure. The sensor can include a first sensor configured to measure intrathecal pressure and a second sensor configured to measure heart rate. The controller can be operable in a learning mode in which no infusion is performed and the controller establishes a correlation between heart rate and intrathecal pressure based on the output of the first and second sensors; and an infusion mode in which the controller coordinates infusion of the drug through the catheter with the intrathecal pulsation of the patient based on the output of the second sensor. The system can include an implantable infusion port in fluid communication with the catheter and an extracorporeal injector configured to mate with the infusion port. The catheter can include first and second fluid lumens. The controller can be configured to control the pump to alternately aspirate fluid through the first fluid lumen and infuse fluid through the second fluid lumen in coordination with the physiological parameter measured by the sensor. The sensor can be configured to measure at least one of heart rate, intrathecal pressure, intrathecal pulsation rate, respiration rate, lung capacity, chest expansion, chest contraction, intrathoracic pressure, and intraabdominal pressure.

In some embodiments, a method of delivering a drug to a patient includes inserting a catheter into an intrathecal space of the patient; measuring a physiological parameter of the patient using a sensor; and with a controller, controlling a pump to coordinate infusion of a drug through the catheter with the physiological parameter measured by the sensor.

The method can include synchronizing infusion frequency with a frequency of the patient's natural intrathecal pulsation as measured by the sensor. The method can include synchronizing infusion phase with a phase of the patient's natural intrathecal pulsation as measured by the sensor. The method can include establishing a sinusoidal approximation of the patient's natural intrathecal pulsation as measured by the sensor and synchronizing infusions with an ascending wave of the sinusoidal approximation. The method can include establishing a sinusoidal approximation of the patient's natural intrathecal pulsation as measured by the sensor and synchronizing infusions with a descending wave of the sinusoidal approximation. The sensor can be configured to measure intrathecal pressure. The sensor can include a first sensor configured to measure intrathecal pressure and a second sensor configured to measure heart rate. The method can include establishing a correlation between heart rate and intrathecal pressure based on the output of the first and second sensors when no infusion is performed; and coordinating infusion of the drug through the catheter with the intrathecal pulsation of the patient based on the output of the second sensor. The catheter can include first and second fluid lumens, and the method can include controlling the pump to alternately aspirate fluid through the first fluid lumen and infuse fluid through the second fluid lumen in coordination with the physiological parameter measured by the sensor. The sensor can be configured to measure at least one of heart rate, intrathecal pressure, intrathecal pulsation rate, respiration rate, lung capacity, chest expansion, chest contraction, intrathoracic pressure, and intraabdominal pressure. The catheter can be inserted such that it extends along the spinal cord of the patient with at least a portion of the catheter being disposed in the cervical region of the patient's spine and at least a portion of the catheter being disposed in the lumbar region of the patient's spine. The method can include delivering a plurality of different drugs through the catheter, each of the drugs being delivered through a respective fluid lumen of the catheter. The method can include, with the controller, controlling the pump to aspirate fluid through the catheter. The catheter can include a plurality of outlet ports spaced in a cranial-caudal direction along the length of the catheter and the method can include infusing a drug through a first port of the catheter and aspirating fluid through a second port of the catheter, the second port being cranial to the first port. The drug can be infused through a port of the catheter disposed in the cervical region of the patient's spine to propel the infused drug into the cranial space. The method can include aspirating a volume of CSF from the patient; infusing a drug through a first, proximal port of the catheter while aspirating CSF through a second, distal port of the catheter to form a bolus of drug between the first and second ports; and infusing the previously-extracted CSF at a location proximal to the bolus to urge the bolus in a distal direction. The volume of CSF aspirated from the patient can be about 10% by volume of the patient's total CSF. The catheter can be inserted through a percutaneous lumbar puncture in the patient. The infusion can include alternating between infusing a first volume of the drug and aspirating a second volume of the drug, the second volume being less than the first volume. The drug can be delivered to a target region, the target region being at least one of an intrathecal space of the patient, a subpial region of the patient, a cerebellum of the patient, a dentate nucleus of the patient, a dorsal root ganglion of the patient, and a motor neuron of the patient. The drug can include at least one of an antisense oligonucleotide, a stereopure nucleic acid, a virus, adeno-associated virus (AAV), non-viral gene therapy, vexosomes, and liposomes. The method can include at least one of performing gene therapy by delivering the drug, performing gene editing by delivering the drug, performing gene switching by delivering the drug, and performing non-viral gene therapy by delivering the drug. The method can include determining a total CSF volume of the patient and tailoring the infusion based on the total CSF volume.

In some embodiments, a method of delivering a drug to a patient includes inserting a catheter into an intrathecal space of the patient; with a controller, controlling a pump to infuse a drug through the catheter; with the controller, controlling the pump to aspirate fluid through the catheter; and controlling said infusion and said aspiration to target delivery of the drug to a target site within the patient.

The infusion can override the natural CSF pulsation of the patient to urge the drug towards the target site. The infusion can coordinate with the natural CSF pulsation of the patient to urge the drug towards the target site. The infusion can include delivering a bolus of the drug and then performing pulsatile delivery of a fluid behind the bolus to urge the bolus towards the target site. The fluid can include at least one of a drug, a buffer solution, and CSF aspirated from the patient through the catheter. At least a portion of the catheter can be disposed in the target region. At least one of the infusion and the aspiration can be coordinated with a physiological parameter of the patient. The physiological parameter can be at least one of heart rate, intrathecal pressure, intrathecal pulsation rate, respiration rate, lung capacity, chest expansion, chest contraction, intrathoracic pressure, and intraabdominal pressure. The catheter can include first and second fluid lumens, and the method can include controlling the pump to alternately aspirate fluid through the first fluid lumen and infuse fluid through the second fluid lumen. The catheter can be inserted such that it extends along the spinal cord of the patient with at least a portion of the catheter being disposed in the cervical region of the patient's spine and at least a portion of the catheter being disposed in the lumbar region of the patient's spine. The method can include aspirating a volume of CSF from the patient; infusing a drug through a first, proximal port of the catheter while aspirating CSF through a second, distal port of the catheter to form a bolus of drug between the first and second ports; and infusing the previously-extracted CSF at a location proximal to the bolus to urge the bolus in a distal direction. The method can include alternating between infusing a first volume of the drug and aspirating a second volume of the drug, the second volume being less than the first volume. The target site can be at least one of an intrathecal space of the patient, a subpial region of the patient, a cerebellum of the patient, a dentate nucleus of the patient, a dorsal root ganglion of the patient, and a motor neuron of the patient. The drug can include at least one of an antisense oligonucleotide, a stereopure nucleic acid, a virus, adeno-associated virus (AAV), non-viral gene therapy, vexosomes, and liposomes. The method can include at least one of performing gene therapy by delivering the drug, performing gene editing by delivering the drug, performing gene switching by delivering the drug, and performing non-viral gene therapy by delivering the drug. The method can include determining a total CSF volume of the patient and tailoring the infusion and/or the aspiration based on the total CSF volume.

In some embodiments, a drug delivery catheter includes a tip having a first fluid lumen that extends to a first fluid port, a second fluid lumen that extends to a second fluid port, and a guidewire lumen; a hub; and a body having a first fluid tube that defines a first fluid lumen that is in fluid communication with the first fluid lumen of the tip, a second fluid tube that defines a second fluid lumen that is in fluid communication with the second fluid lumen of the tip, a guidewire having a distal end disposed within the guidewire lumen of the tip, and a sheath that defines at least one interior channel in which the guidewire and the first and second fluid tubes are disposed, wherein the sheath extends from a distal end of the hub to a proximal end of the tip.

The tip can have a tapered distal end. The first and second fluid ports can be offset from a central longitudinal axis of the tip. At least one of the first and second fluid ports can be aimed perpendicular to, or at an oblique angle with respect to, the central longitudinal axis of the tip. The first and second fluid tubes can extend uninterrupted through the hub. The first and second fluid tubes can terminate within the hub at respective connectors to which proximal extension tubes can be selectively coupled. The guidewire can extend uninterrupted through the hub. The first and second fluid tubes can have respective fluid connectors at proximal ends thereof. At least one of the first and second fluid tubes can be formed from fused silica. At least one of the first and second fluid tubes can be coated in shrink tubing. The sheath can be formed form polyurethane. The sheath can include an opening formed therein in fluid communication with a fluid port of at least one of the first and second fluid tubes. At least one of the first and second ports can have a helical interior. At least one of the first and second ports can have an interior that tapers towards the distal end of the port. The first fluid port can be proximal to the second fluid port. The catheter can include an auger rotatably mounted within the catheter. The catheter can include a piezoelectric transducer disposed within the catheter.

In some embodiments, a percutaneous needle device includes an elongate shaft that defines at least one lumen therein; a sensor disposed at a distal end of the elongate shaft; a display mounted to the elongate shaft configured to display an output of the sensor; and a connector disposed at a proximal end of the elongate shaft for making a fluid connection with the at least one lumen.

The device can include a fluid reservoir and a flush dome in fluid communication with the lumen of the needle, wherein actuation of the flush dome is effective to pump fluid from the reservoir through the lumen of the needle.

In some embodiments, a catheter includes an elongate body having one or more fluid lumens formed therein; and a fluid port formed in the catheter, the fluid port being defined by a helical slit formed in a wall of the catheter.

The catheter can include an atraumatic distal tip defined by a substantially spherical bulb. The catheter can include a second, distal-facing fluid port. The helical slit can be formed in a sidewall of a reduced-diameter portion of the catheter. The catheter can include a tapered transition between a main body of the catheter and a reduced-diameter portion of the catheter.

In some embodiments, a patient-specific infusion method includes determining a total CSF volume of a patient; aspirating a volume of CSF from the patient based on the determined total CSF volume of the patient; and infusing a drug into an intrathecal space of the patient.

The method can include, after infusing the drug, infusing the aspirated CSF of the patient to push the drug in a desired direction within the intrathecal space. The total CSF volume can be determined from a pre-operative image of the patient's central nervous system. The aspirated volume of CSF can be in the range of about 1% to about 20% of the total CSF volume of the patient. The drug can be infused while the volume of CSF is aspirated.

BRIEF DESCRIPTION OF THE DRAWINGS

FIG. 19 is a screen capture of a graphical user interface that can be implemented by the controller of FIG. 17;

DETAILED DESCRIPTION

Figure 1:
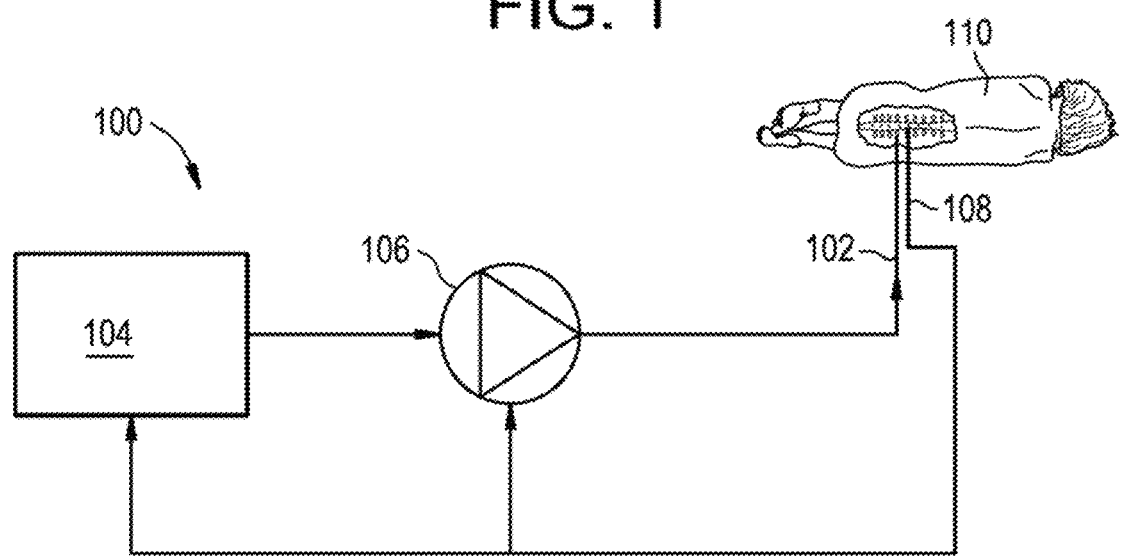
FIG. 1 is a schematic view of a drug delivery system.

Drug delivery systems and methods are disclosed herein. In some embodiments, a drug delivery system can be configured to deliver a drug to a patient in coordination with a physiological parameter of the patient (e.g., the patient's natural cerebrospinal fluid (CSF) pulsation or the patient's heart or respiration rate). In some embodiments, a drug delivery system can be configured to use a combination of infusion and aspiration to control delivery of a drug to a patient. Catheters, controllers, and other components for use in the above systems are also disclosed, as are various methods of using such systems.

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

In some embodiments, systems and methods are provided in which a drug is injected or otherwise delivered to the central nervous system of a patient in coordination with the natural CSF flow. For example, the drug can be injected in a plurality of stages synchronized in phase and/or frequency with the natural CSF pulse. The systems and methods herein can allow for a drug to be delivered more efficiently to a patient than in the case of traditional techniques. For example, a smaller quantity of the drug can be delivered and still reach the target destination, thereby reducing cost and/or possible side effects of delivering a large quantity of the drug.

The systems and methods disclosed herein can be used in applications where the intended delivery target is not accessible or not accessible in a minimally-invasive manner, but instead more readily-accessible and safer injection sites which are in direct fluid communication with the intended delivery site exist. For example, a drug can be delivered to the intrathecal space of a patient via an injection site in the patient's spine (e.g., a lumbar region, a thoracic region, a cervical region, and so forth) and can be transported via the intrathecal space to a target location that is cranial to the injection site (e.g., the brain or a more-cranial region of the spine). In other embodiments, the drug can be transported to a location that is caudal to the injection site.

The systems and methods disclosed herein can include fully programmable customized injection and/or aspiration profiles which can be synchronized by real-time monitoring of physiological parameters of the patient, such as heart rate, CSF pressure, CSF pulsation rate, respiration rate, lung capacity, chest expansion and contraction, intrathoracic pressure, intraabdominal pressure, and the like. This can allow the end user to fine-tune injection/aspiration doses per cycle, time length and profile of each microinjection, relative timing (or phase) of microinjections, and other parameters. The systems and methods disclosed herein can include real-time inline pressure sensing for estimating drug delivery efficiency and ensuring patient safety.

The systems and methods disclosed herein can include custom built catheters with various lumen quantities, lumen sizes, port placement locations, and other properties. The catheters can be directionality-optimized for efficient mixing and/or such that they are adapted for a particular anatomy.

FIG. 1 is a schematic diagram of an exemplary drug delivery system 100. As shown, the system 100 can include a catheter 102, a controller 104, a pump or actuator 106, and one or more sensors 108. The pump 106 can be configured to pump a drug or a drug-containing fluid through the catheter 102 and into a patient 110 (e.g., into an intrathecal space of the patient). The pump 106 can also be configured to aspirate fluid from the patient. The pump 106 can be controlled by the controller 104 to synchronize or otherwise coordinate delivery of the drug and/or aspiration of fluid with a physiological parameter of the patient, which can be measured by the sensor 108. Exemplary physiological parameters can include heart rate, CSF pressure, CSF pulsation rate, respiration rate, lung capacity, chest expansion and contraction, intrathoracic pressure, intraabdominal pressure, and the like.

Figure 2:
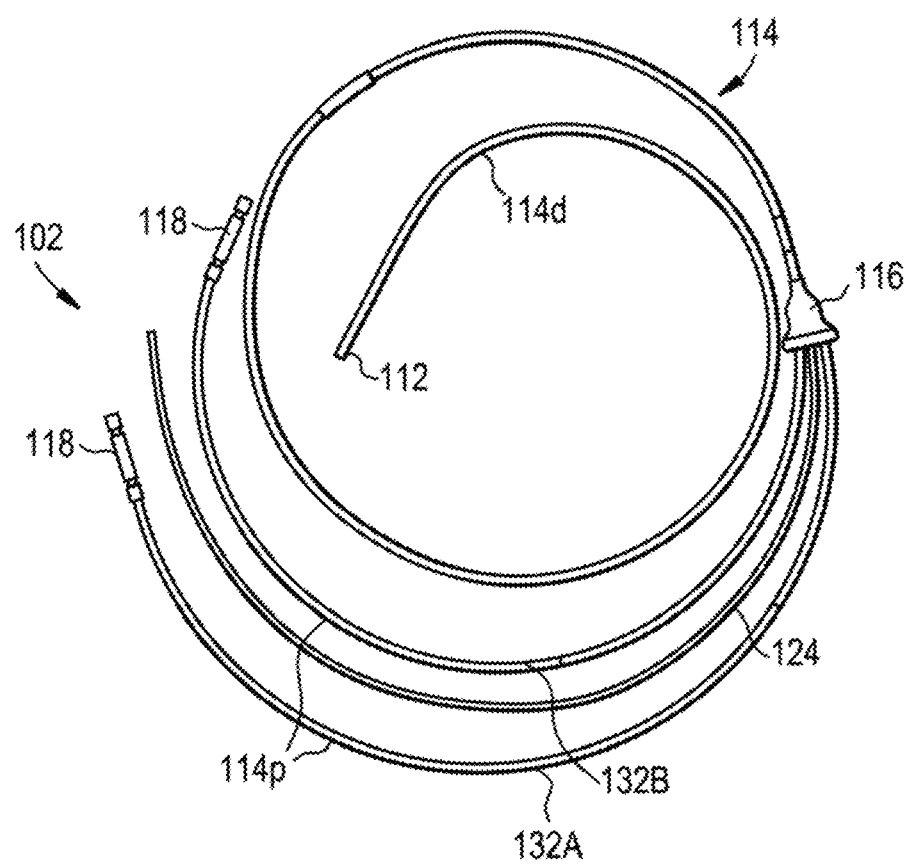
FIG. 2 is a perspective view of a catheter that can be used with the system of FIG. 1.

An exemplary catheter 102 which can be used with the system 100 is shown in FIG. 2. The catheter 102 can include a tip portion 112, a body 114, and a hub 116. A first portion 114d of the body 114 can extend between the tip 112 and the distal end of the hub 116. A second portion 114p of the body 114 can extend proximally from the hub 116 to one or more connectors 118 or other features for coupling the catheter 102 to the system 100, e.g., for attaching the catheter to the pump 106. The catheter 102 can have an overall length of about 1 meter.

Figure 3A:
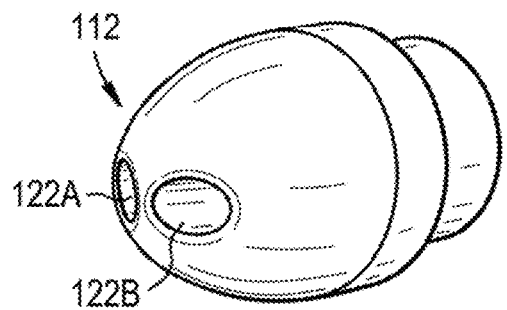
FIG. 3A is a perspective view of a tip of the catheter of FIG. 2.
Figure 3B:
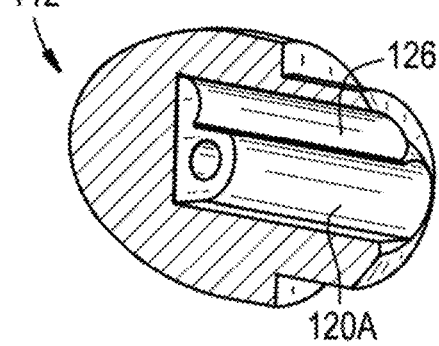
FIG. 3B is a sectional view of the tip of the catheter of FIG. 2.
Figure 3C:
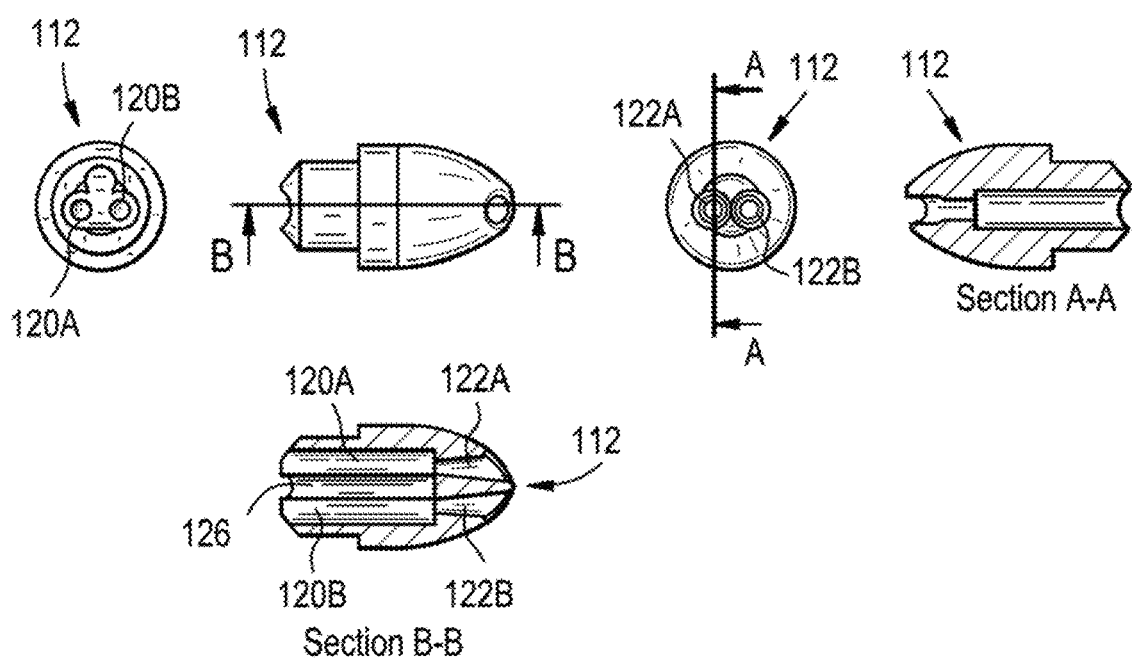
FIG. 3C is a series of design views of the tip of the catheter of FIG. 2.

The tip 112 of the catheter 102 is shown in more detail in FIGS. 3A-3C. The tip 112 can include a generally cylindrical body with a conical, bulleted, or tapered tip. The tip 112 can provide an atraumatic lead-in surface to facilitate tunneling the catheter 102 through tissue or through a lumen of the patient, such as the intrathecal space. The tip 112 can include one or more fluid lumens formed therein, and a corresponding one or more fluid ports through which fluid can be communicated from the fluid lumen to an exterior of the catheter and vice-versa. In the illustrated embodiment, the tip 112 includes a first fluid lumen 120A with a first fluid port 122A and a second fluid lumen 120B with a second fluid port 122B, though it will be appreciated that the tip can include any number of fluid lumens (e.g., zero, one, two, three, four, five, more than five, etc.) and any number of fluid ports (e.g., zero, one, two, three, four, five, more than five, etc.). The fluid ports 122A, 122B can be aimed in a substantially distal direction and can be offset from the central longitudinal axis of the tip 112, as shown. In other embodiments, the fluid ports 122A, 122B can be aimed laterally, e.g., in a direction substantially perpendicular to the central longitudinal axis of the tip 112. Having the fluid ports slightly offset from center or aimed laterally can advantageously reduce the risk of the ports becoming occluded during insertion or use of the catheter 102.

The catheter 102 can include a steering mechanism to facilitate remote positioning of the catheter within the patient. For example, the catheter 102 can be configured to receive a guidewire 124 therethrough to allow the catheter to be inserted over the guidewire or to be steered by the guidewire. In the illustrated embodiment, the tip 112 includes a guidewire lumen 126. The guidewire lumen 126 can be a closed, blind hole as shown, or can be open to an exterior of the tip 112. Alternatively, or in addition, the catheter 102 can include one or more steering wires (not shown) that terminate at the tip 112. The wires can extend proximally from the tip 112 to a proximal end of the catheter 102, where they can be selectively tensioned to steer the tip of the catheter within the patient. For example, the catheter 102 can include first and second steering wires that extend longitudinally therethrough and which are anchored to the tip 112 at diametrically-opposed locations about the outer periphery of the tip. The steering wires can extend through respective sleeves or tubes in the body 114 of the catheter 102 to the proximal end of the catheter where tension can be selectively applied thereto to steer the tip 112 of the catheter.

The tip 112 can be formed from various materials, including biocompatible materials, stainless steel, titanium, ceramics, polymers, and the like. The tip 112 can be radiopaque or can include one or more radiopaque markers to facilitate visualization under fluoroscopy or other imaging techniques.

The tip 112 can have an outside diameter of about 3 French to about 5 French. The tip 112 can have an outside diameter of about 1 mm to about 3 mm.

Figure 4:
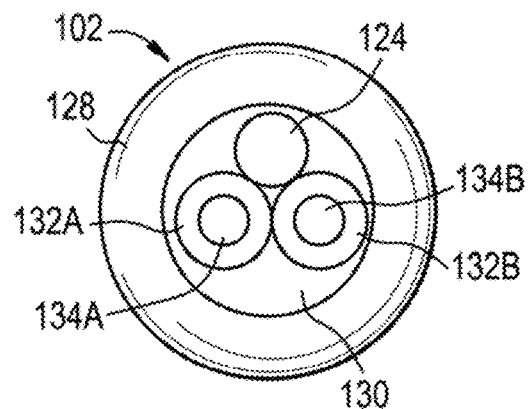
FIG. 4 is a sectional view of a body of the catheter of FIG. 2.

FIG. 4 is a cross-sectional view of the distal portion 114d of the catheter body 114. As shown, the body 114 can include an outer sheath 128 that defines an interior channel 130. One or more fluid tubes 132A, 132B can be disposed within the interior channel, each fluid tube defining a respective fluid lumen 134A, 134B. The interior channel 130 can also contain a guidewire 124 or one or more steering wires (not shown). In the illustrated embodiment, the distal body portion 114d includes a first fluid tube 132A having a lumen 134A in fluid communication with the first fluid lumen 120A of the tip 112, a second fluid tube 132B having a lumen 134B in fluid communication with the second fluid lumen 120B of the tip, and a guidewire 124.

The sheath 128 can have various cross-sectional profiles. For example, the sheath 128 can have a circular transverse cross-section that defines a single interior channel 130 as shown. By way of further example, the sheath 128 can have multiple interior channels. Each of the fluid tubes 132A, 132B can be disposed within its own independent channel of the sheath 128, or the sheath itself can define the fluid tubes. The guidewire 124 can be disposed in its own independent channel of the sheath 128 and the fluid tubes 132A, 132B can be disposed in a separate channel of the sheath. The guidewire channel can have a circular cross-section and the fluid tube channel can have a crescent or D-shaped cross-section.

The fluid tubes 132A, 132B can be formed from any of a variety of materials, including fused silica, polyurethane, etc. Use of fused silica can be advantageous when using the system 100 to deliver viruses, as viruses may be less prone to sticking to fused silica fluid tubes. In some embodiments, fluid tubes used for drug delivery can be formed from fused silica and fluid tubes not used for drug delivery (e.g., buffer delivery tubes or aspiration tubes) can be formed from a material other than fused silica, such as polyurethane. The fluid tubes 132A, 132B can be coated with a shrink tubing or an outer sheath to provide stress and strain relief for the fluid tubes. The sheath 128 can be formed from any of a variety of materials, including polyurethane. While use of the fluid tubes 132A, 132B to communicate fluid is generally described herein, the fluid tubes can also be used for other purposes, such as inserting a biopsy probe or other instrument, or inserting a sensor 108.

The fluid tubes 132A, 132B can have an inside diameter of about 0.005 inches to about 0.050 inches. The fluid tubes 132A, 132B can have an inside diameter of about 0.010 inches to about 0.020 inches. The body 114 can have an outside diameter of about 3 French to about 5 French. The body 114 can have an outside diameter of about 1 mm to about 3 mm.

Figure 5:
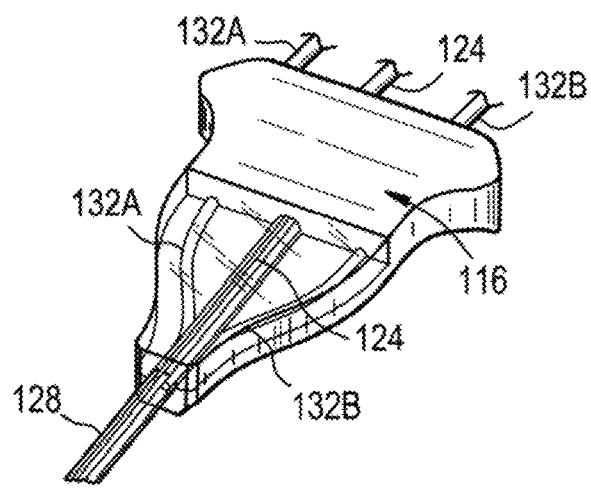
FIG. 5 is a perspective view of a hub of the catheter of FIG. 2, with a portion of the hub shown as transparent.

An exemplary hub 116 is shown in FIG. 5. The hub 116 can include respective channels for receiving the first fluid tube 132A, the second fluid tube 132B, and the guidewire 124. Each channel can include proximal and distal openings. The channels can merge within the body of the hub 116 such that they each share a common distal opening. The sheath 128 of the distal body portion 114d can be received through the distal opening of the hub 116 and into the guidewire channel of the hub. The fluid tubes 132A, 132B can penetrate the sidewall of the sheath 128 within the body of the hub 116. The hub 116 can thus form a seal between the sheath 128 and the fluid tubes 132A, 132B, support the fluid tubes and the guidewire 124, and guide these components into the inner channel(s) 130 of the sheath of the distal body portion 114d.

Figure 6A:
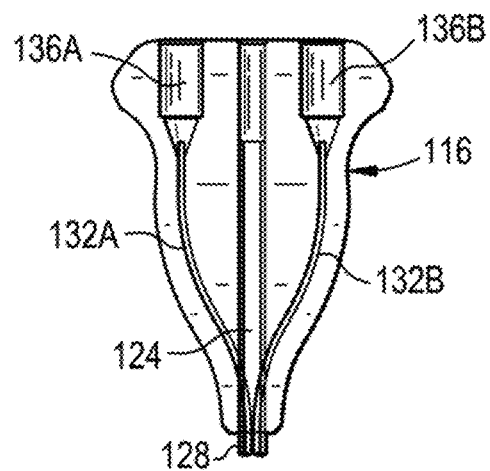
FIG. 6A is a sectional view of the hub of FIG. 5, shown with integrated connectors.
Figure 6B:
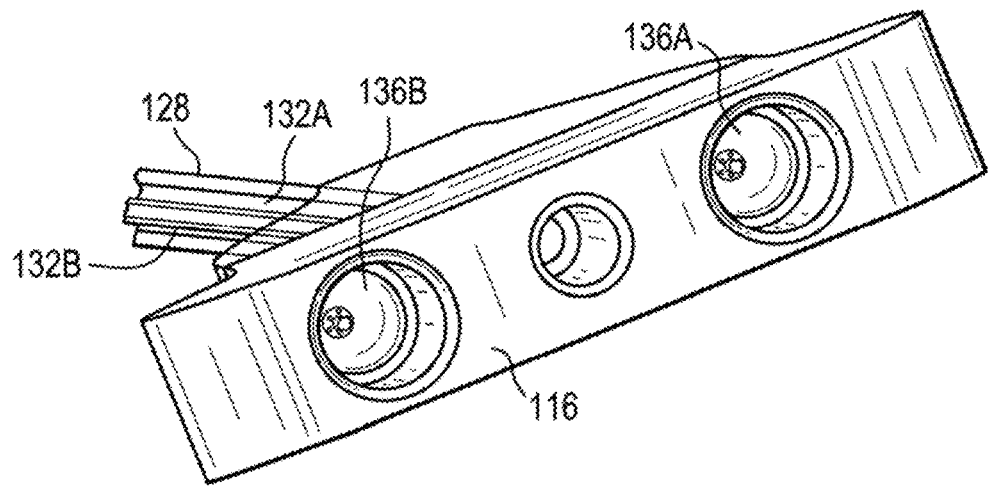
FIG. 6B is an end view of the hub of FIG. 5, shown with integrated connectors.

The hub 116 can be a "pass-through" type hub in which the first and second fluid tubes 132A, 132B extend completely through the hub uninterrupted as shown in FIG. 5. Alternatively, as shown in FIGS. 6A-6B, the first and second fluid tubes 132A, 132B can terminate within the hub at respective connector ports 136A, 136B. The connector ports 136A, 136B can allow selective coupling and decoupling of the proximal body portion 114p (e.g., proximal extension tubes) to the first and second fluid tubes 132A, 132B. The guidewire 124 can continue to extend completely through the hub 116 uninterrupted, or it too can terminate within the hub at a connector where a proximal guide wire extension can be selectively coupled thereto. Any of a variety of connector types can be used to couple the fluid tubes to the proximal extension tubes, including zero-dead-volume micro-connectors or fittings available from Valco Instruments Co. Inc. of Houston, Tex.

The proximal body portion 114p can include a sheath similar to that of the distal body portion 114d, or can be formed by the fluid tubes 132A, 132B extending proximally from the hub 116, or from one or more extension tubes coupled to the fluid tubes 132A, 132B at the hub 116. The proximal end of the catheter 102 can include one or more connectors 118 for making a fluid connection with the fluid tubes 132A, 132B of the catheter. For example, as shown in FIG. 2, the fluid tubes 132A, 132B (or proximal extension tubes as the case may be) can include a connector 118 at a proximal end thereof. Any of a variety of connector types can be used, including zero-dead-volume micro-connectors or fittings available from Valco Instruments Co. Inc. of Houston, Tex.

The guidewire 124 can be disposed within the catheter 102 and can be used to guide, steer, or otherwise control insertion of the catheter into the patient.

The guidewire 124 can be cylindrical and can have a substantially-straight profile. The guidewire 124 can extend completely through the catheter 102, or can terminate in a blind bore 126 formed in the tip 112 of the catheter. In use, the guidewire 124 can be inserted into the patient first and guided to a target site, and the catheter 102 can then be inserted over the guidewire to position a portion of the catheter at the target site. In other embodiments, the catheter 102 can be inserted before or simultaneously with the guidewire 124, and the guidewire can be used to steer or guide the catheter.

Figures 7A, 7B, 7C:
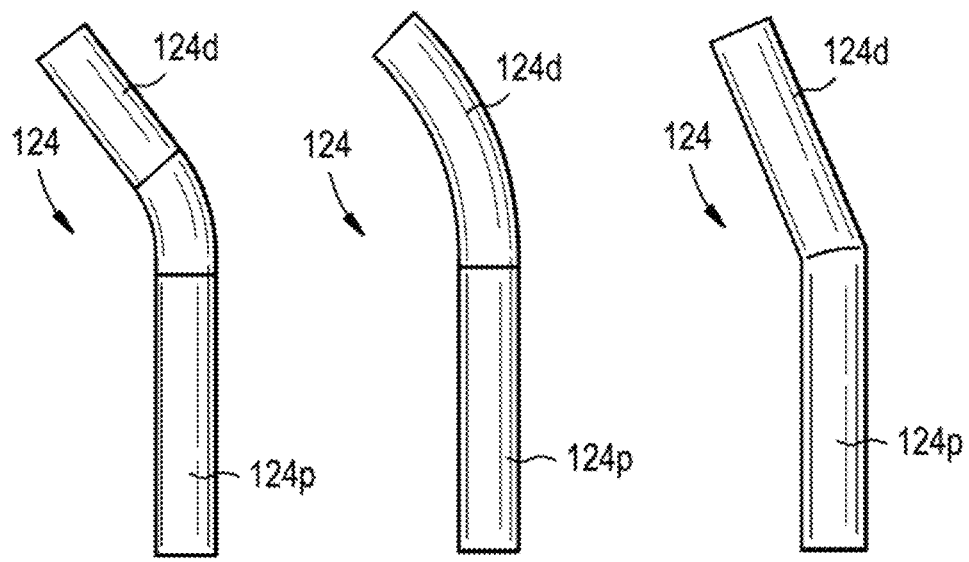
FIG. 7A is a plan view of a first bend profile of a guidewire of the catheter of FIG. 2.
FIG. 7B is a plan view of a second bend profile of a guidewire of the catheter of FIG. 2.
FIG. 7C is a plan view of a third bend profile of a guidewire of the catheter of FIG. 2.

For example, as shown in FIGS. 7A-7C, the guidewire 124 can have a resting configuration that deviates from a straight line at or near a distal end of the guidewire. In FIG. 7A, the guidewire 124 has a straight distal portion 124d and a straight proximal portion 124p joined by a curved elbow such that a central longitudinal axis of the distal portion extends at an oblique angle with respect to a central longitudinal axis of the proximal portion. In FIG. 7B, the guidewire 124 has a curved distal portion 124d joined to a straight proximal portion 124p such that a central longitudinal axis of the distal portion extends at an oblique angle with respect to a central longitudinal axis of the proximal portion. In FIG. 7C, the guidewire 124 has a straight distal portion 124d and a straight proximal portion 124p that meet at an angled bend such that a central longitudinal axis of the distal portion extends at an oblique angle with respect to a central longitudinal axis of the proximal portion.

In use, the guidewire 124 can be used to navigate the catheter 102 through the patient by twisting the proximal end of the guidewire to turn the bent distal portion and thereby steer or aim the catheter. While a single guidewire 124 is shown, it will be appreciated that the catheter 102 can include any number of guidewires and/or guidewire lumens. The guidewire 124 can be formed from any of a variety of materials, including shape-memory metals such as Nitinol.

Any of the catheters disclosed herein can be steerable. For example, a steering mechanism can be provided to allow the distal end of the catheter 102 to be guided during insertion or at another desired time. In some embodiments, the catheter 102 can include one or more steering wires having a first end coupled to the distal tip 112 of the catheter and having a second end at the proximal end of the catheter through which tension can be selectively applied to the steering wires to direct or steer the tip of the catheter in a desired direction. The steering wires can be embedded in the sidewalls of the catheter 102 or can extend through a lumen of the catheter.

In some embodiments, the catheter 102 can include a coaxial steering catheter (not shown) extending therethrough. A distal end of the steering catheter can be curved or biased towards a curved shape such that, when the steering catheter is deployed distally from the tip of the primary catheter 102, the primary catheter can be steered or guided along the curve of the steering catheter. The steering catheter can then be retracted back into the primary catheter 102 to discontinue the curved guidance. The steering catheter can be formed from or can include shape memory or resilient materials such that the steering catheter is deformable between a substantially straight line configuration when retracted into the primary catheter 102 and a flexed or curved configuration when deployed from the primary catheter. The steering catheter can be longitudinally translatable relative to the primary catheter 102 to allow for deployment and retraction.

Any of the catheters disclosed herein can include a camera or imaging device, which can be integral with the catheter or can be inserted through a working channel of the catheter. Any of the catheters disclosed herein can include markings visible under fluoroscopy, CT, MRI, or other imaging techniques to allow the catheter to be visualized in images captured using such techniques.

The catheter 102 can be configured to withstand high internal pressures. The catheter 102 can be configured to withstand a pressure of at least about 100 psi, at least about 200 psi, and/or at least about 500 psi.

Figure 8A:
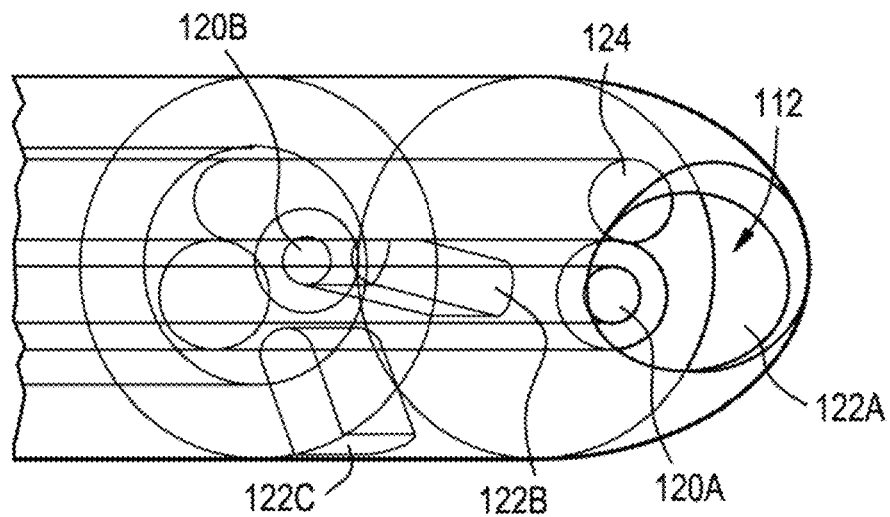
FIG. 8A is a perspective, partially-transparent view of a tip that can be used with the catheter of FIG. 2.
Figure 8B:
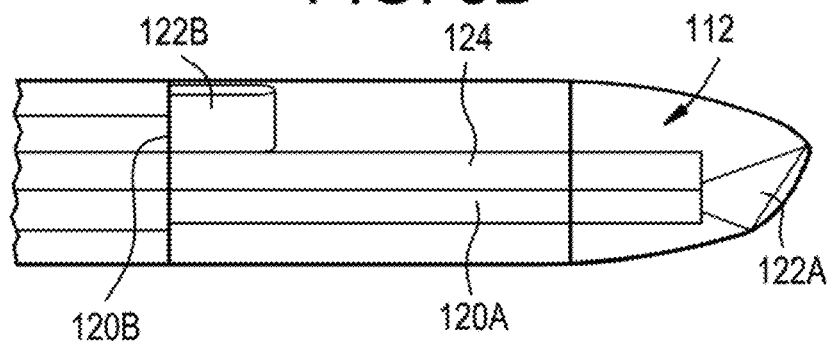
FIG. 8B is a profile, partially-transparent view of the tip of FIG. 8A.

It will be appreciated that a number of variations on the above-described catheter 102 are possible. For example, one or more of the fluid ports can be aimed to the side such that they exit a lateral sidewall of the catheter. FIGS. 8A-8B illustrate an exemplary catheter tip having side-facing ports. As shown, the tip 112 includes a first fluid lumen 120A that extends to a distal-facing port 122A. The distal-facing port 122A can be formed in an angled or slash-cut distal face of the tip 112. The tip 112 also includes a second fluid lumen 120B that extends to a side-facing port 122B. The tip 112 can also include a guidewire lumen for receiving the distal end of a guide wire 124. In some embodiments, the central channel 130 of the sheath 128 can act as a fluid lumen, e.g., for delivering a buffer or for delivering a drug. The tip 112 can include a side-facing port 122C in fluid communication with the central channel 130 of the sheath 128.

Figure 9:
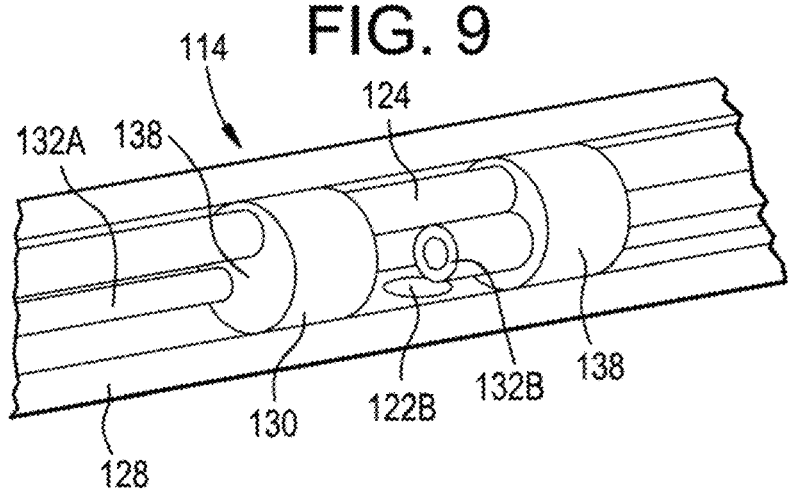
FIG. 9 is a perspective, partially-transparent view of the body of the catheter of FIG. 2, shown with a side exit port.

The catheter 102 can include one or more fluid ports formed proximal to the tip portion 112 of the catheter, e.g., formed in the body 114 of the catheter. FIG. 9 illustrates an exemplary catheter body 114 having a side-facing port 122B. As shown, one or more of the fluid tubes 132A, 132B extending through the sheath 128 of the body 114 can terminate within the body or can otherwise have a fluid port disposed in the body. The sheath 128 can have a slit or opening 122B aligned with the port of the fluid tube 132B, such that fluid exiting the fluid tube can flow through the opening in the sheath or such that fluid can flow through the sheath and into the port of the fluid tube. The catheter 102 can include one or more plugs 138 disposed within the channel 130 of the sheath 128 to prevent fluid exiting or entering the fluid tube 132B from flowing proximally and/or distally within the sheath, instead guiding the fluid out of the sheath through the opening or slit 122B formed therein, or guiding incoming fluid into the fluid port of the tube. The plugs 138 can be formed from a rigid material, from an adhesive, silicone, or various other materials.

Figure 10:
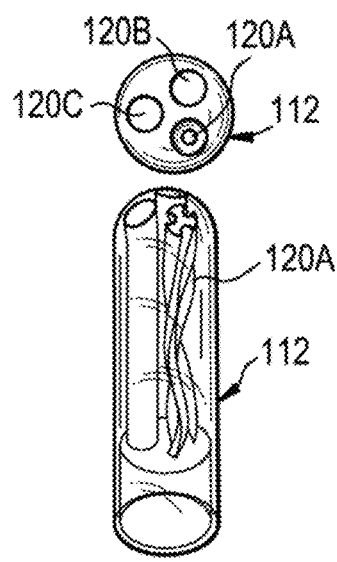
FIG. 10 is a perspective and end view of a tip that can be used with the catheter of FIG. 2.
Figure 11:
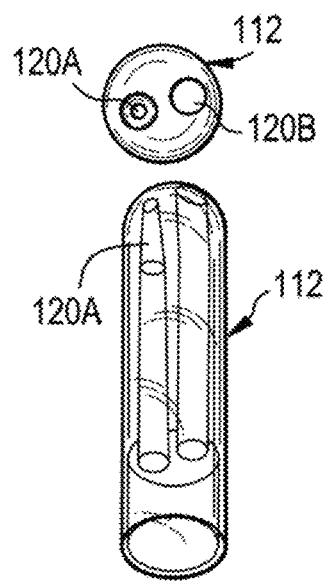
FIG. 11 is a perspective and end view of a tip that can be used with the catheter of FIG. 2.

The fluid lumens of the catheter can have various internal geometries to control or direct the delivery pattern of fluid delivered therethrough. FIG. 10 illustrates an exemplary catheter tip 112 in which one of the fluid lumens 120A has a thread formed on an interior surface thereof to define a helical or "corkscrew" shape. The helical shape of the fluid lumen 120A can promote turbulent flow of fluid therefrom encouraging dispersion or even distribution of the fluid. It will be appreciated that more than one of the fluid lumens can have a helical tip. FIG. 11 illustrates an exemplary catheter tip 112 in which one of the fluid lumens 120A tapers or narrows towards the distal end to create a nozzle. This nozzle can create a jet-stream effect, increasing the velocity of the infusate as it is delivered. It will be appreciated that more than one of the fluid lumens can have a nozzle tip. As also shown in FIGS. 10-11, one or more of the fluid lumens can have a simple cylindrical tip.

As noted above, the catheter 102 can include any number of lumens extending therethrough. In some embodiments, a dual-lumen catheter can be used. The dual lumen catheter can include an infusion lumen and a pressure sensor lumen, an infusion lumen and an aspiration lumen, two infusion lumens, etc. In other embodiments, a tri-lumen catheter can be used. The tri-lumen catheter can include an infusion lumen, an aspiration lumen, and a pressure sensor lumen, two infusion lumens and an aspiration lumen, three infusion lumens, etc. FIG. 10 illustrates an exemplary tri-lumen catheter having an infusion lumen 120A, an aspiration lumen 120B, and a pressure sensor lumen 120C. FIG. 11 illustrates an exemplary dual-lumen catheter an infusion lumen 120A and an aspiration lumen 120B.

The catheter can include a valve system to control the direction of fluid flow therethrough. For example, a valve system can include one-way valves on each lumen to prevent infusion into an aspiration lumen and vice versa. The valve system can facilitate use of a single syringe or other pump to infuse and withdraw fluid, or can facilitate infusion and aspiration through a single lumen.

As discussed further below, the sensor 108 can be mounted to the catheter 102, formed integrally with the catheter, threaded through a lumen of the catheter, etc. For example, the catheter 102 can include a sensor 108 embedded in the tip portion 112 of the catheter, or can include a sensor threaded through a dedicated sensor lumen of the catheter.

Figure 12:
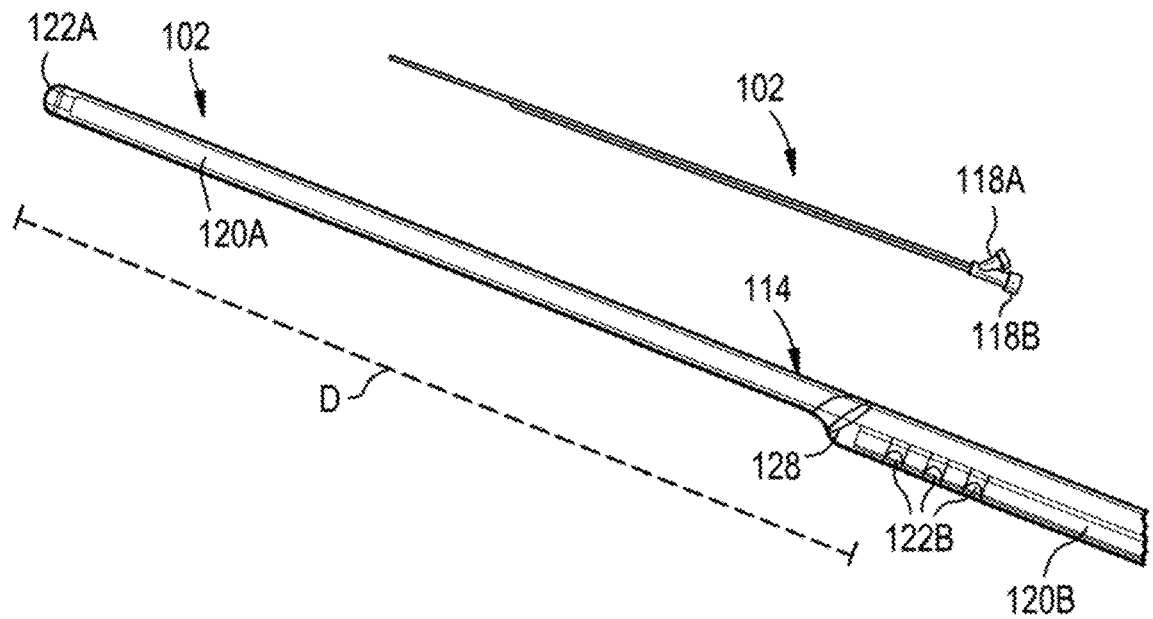
FIG. 12 is a perspective view with a detail, partially-transparent inset of a catheter that can be used with the system of FIG. 1.

One or more of the fluid lumens through the catheter can have fluid ports that are longitudinally offset from fluid ports of other lumens of the catheter. For example, as shown in FIG. 12, the catheter 102 can include a first fluid lumen 120A that extends to a fluid port 122A formed at the terminal distal end of the catheter. The catheter 102 can also include a second fluid lumen 120B that extends to fluid ports 122B which are spaced a distance D apart from the distal end of the catheter in a proximal direction. As shown, the second fluid lumen 120B can include one or more side-facing ports 122B. In other embodiments, the second fluid lumen 120B can include a distal facing port. In use, one of the fluid lumens 120A, 120B can be used to deliver a drug or other fluid and the other fluid lumen can be used to aspirate fluid from the patient. The catheter 102 can thus be used to create a "push-pull" effect at a target site, in which a drug is infused at the distal end of the catheter via the first fluid lumen 120A and then drawn back toward the proximal end of the catheter by the flow of fluid being aspirated through the second fluid lumen 120B. The opposite arrangement can also be used, in which the drug is infused through the proximal port(s) and aspirated through the distal port(s). A proximal end of the catheter 102 can have first and second connectors 118A, 118B corresponding respectively to the first and second fluid lumens 120A, 120B. The offset fluid ports 122A, 122B can be used to coordinate delivery with a physiological parameter of the patient, such as natural CSF flow. An external peristaltic pump or other device can be used to drive the infusion and/or aspiration. As shown, the outer sheath 128 of the body 114 can taper inward to the first lumen 120A after the termination of the second lumen 120B.

Figure 13:
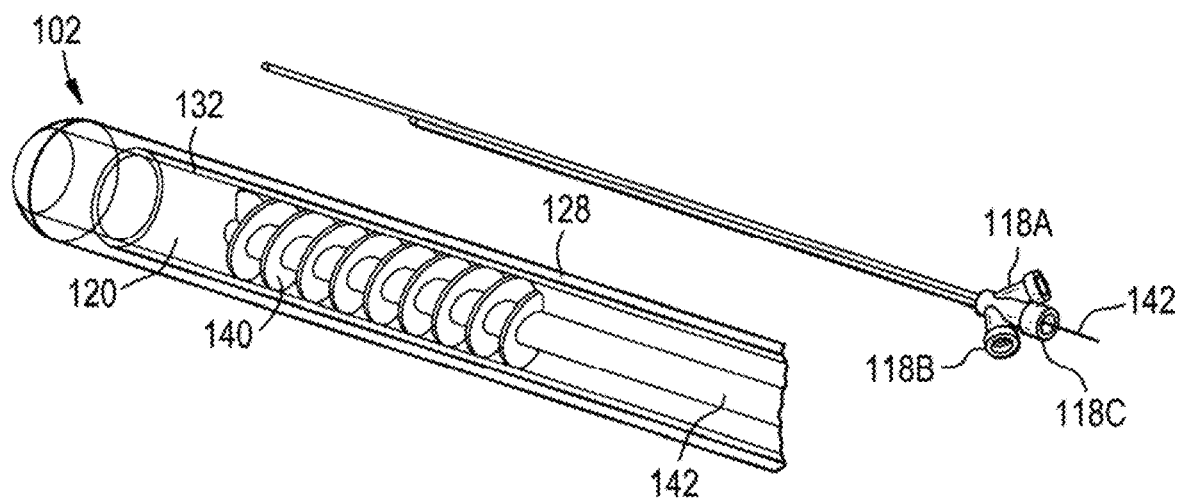
FIG. 13 is a perspective view with a detail, partially-transparent inset of a catheter that can be used with the system of FIG. 1.

The catheter 102 can include features for controlling delivery of fluid through the catheter. For example, as shown in FIG. 13, the catheter 102 can include an internal auger 140. The auger 140 can have an elongate flexible shaft 142 that extends through the catheter 102 to a proximal end of the catheter, where it can be coupled to a motor for driving rotation of the auger. The motor can be part of the controller 104 or can be a separate component. The controller 104 can start and stop rotation of the auger 140, and/or can control the speed or direction of auger rotation to control delivery of fluid through the fluid lumen 120 in which the auger is disposed. The auger 140 can be disposed in a fluid tube 132 extending through a sheath portion 128 of the catheter 102. The auger 140 can also be disposed distal to a terminal distal end of a fluid tube 132, with the auger shaft 142 extending through the fluid tube. The auger 140 can thus be disposed within the sheath 128 of the catheter 102 but distal to a fluid tube 132 of the catheter. The auger 140 can advantageously control fluid delivery through the catheter 102 and generate more turbulent flow of fluid from the catheter. A proximal end of the catheter can have first and second connectors 118A, 118B corresponding respectively to the first and second fluid lumens and a third port or connector 118C through which the auger shaft 142 can extend. The auger 140 can be used to coordinate delivery with a physiological parameter of the patient, such as natural CSF flow.

Figure 14:
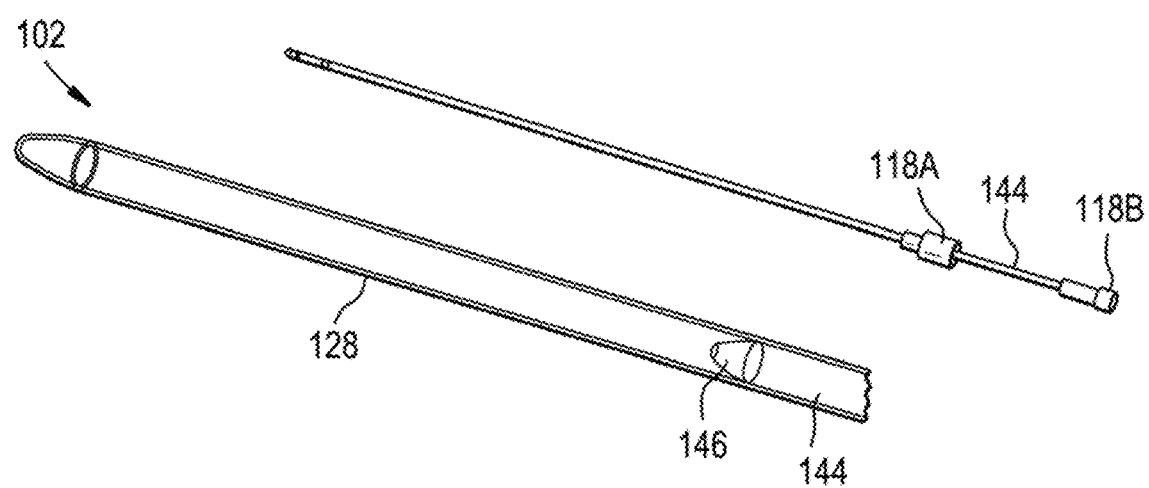
FIG. 14 is a perspective view with a detail, partially-transparent inset of a catheter that can be used with the system of FIG. 1.

By way of further example, as shown in FIG. 14, the catheter 102 can include an internal, reciprocating piston or inner tube 144. The catheter 102 can include a fixed outer tube 128 and a slidable inner tube 144 disposed coaxially within the outer tube. The inner tube 144 can be configured to translate longitudinally with respect to the outer tube 128. The inner tube 144 can include a valve 146, e.g., at a terminal distal end thereof. Exemplary valves include one-way valves, duck-bill valves, spring-biased check valves, and the like. A seal can be formed between the inner tube 144 and the outer tube 128, e.g., at a proximal end of the catheter 102. In use, the inner tube 144 can be loaded with a drug-containing fluid. The inner tube 144 can then be pulled proximally with respect to the outer tube 128 to cause the drug-containing fluid to flow through a one-way valve 146 into the distal end of the outer tube. The inner tube 144 can then be pushed distally, closing the one-way valve 146 and expelling the drug-containing fluid out of the distal end of the outer tube 128 and into the patient. The translating tubes 128, 144 can allow a fixed or predetermined volume of drug-containing infusate to be delivered with each reciprocation of the inner tube 144. The proximal ends of the outer and inner tubes 128, 144 can include connectors 118A, 118B, e.g., for supplying fluid to the outer and inner tubes. The reciprocating inner tube 144 can be used to coordinate delivery with a physiological parameter of the patient, such as natural CSF flow.

Figure 15:
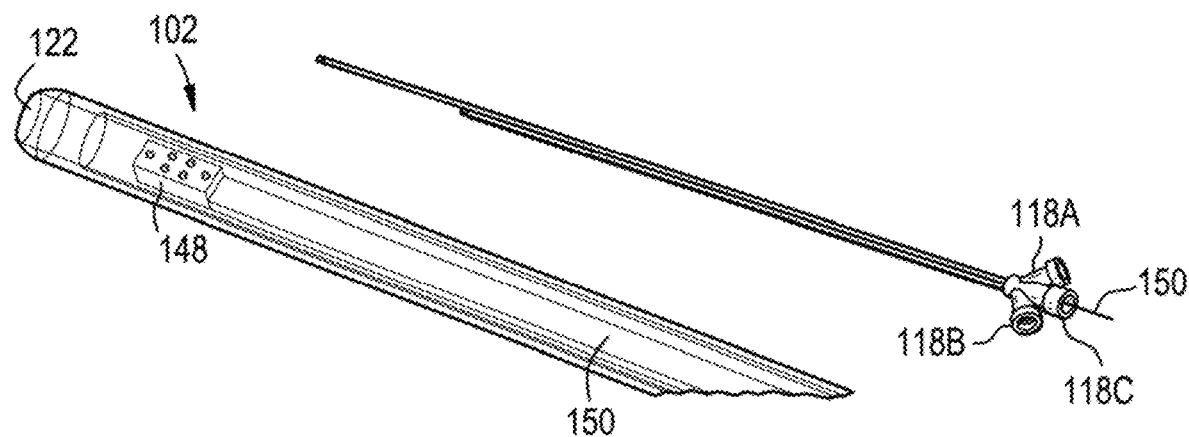
FIG. 15 is a perspective view with a detail, partially-transparent inset of a catheter that can be used with the system of FIG. 1.

As another example, as shown in FIG. 15, the catheter 102 can include a transducer 148, such as a piezoelectric transducer, to help control delivery of a drug through the catheter. The transducer 148 can be formed on a flex circuit or other substrate disposed adjacent to a fluid port 122 of the catheter 102. The transducer 148 can include an electrically-conductive lead or wire 150 that extends proximally therefrom through the catheter 102 to the controller 104. In use, an electric potential can be applied to the transducer 148 to induce vibration or other movement of the transducer. This movement can control distribution of the drug from the catheter 102. For example, the transducer 148 can control the direction in which the infusate flows as it exits the catheter 102, can control the opening or closing of a fluid port 122 of the catheter, and/or can control the volume of infusate that exits the catheter. A proximal end of the catheter 102 can have first and second connectors 118A, 118B corresponding respectively to first and second fluid lumens and a third port or connector 118C through which the electrical conductor 150 of the transducer 148 can extend. The transducer 148 can be used to coordinate delivery with a physiological parameter of the patient, such as natural CSF flow.

Figure 16:
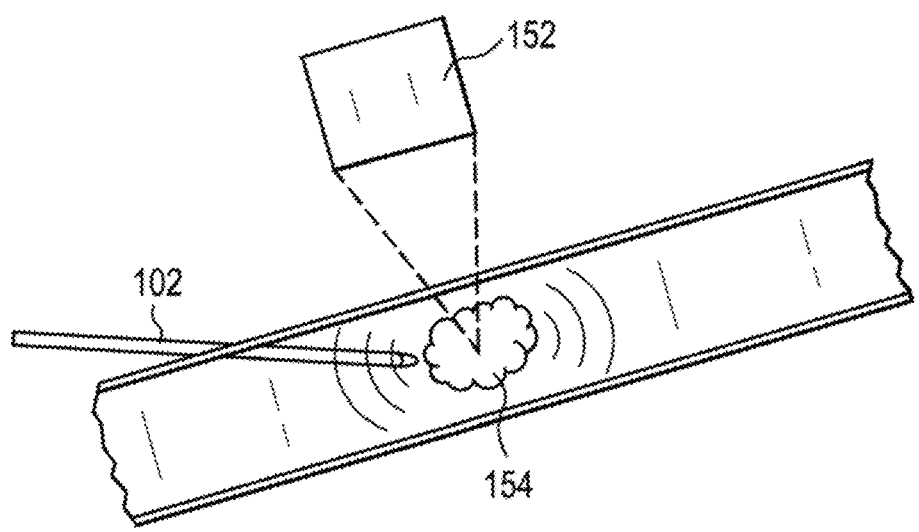
FIG. 16 is a schematic view of a focused ultrasound system that can be used with the system of FIG. 1.

The system 100 can include one or more transducers for delivering focused ultrasound to the patient. As shown in FIG. 16, a focused ultrasound system 152 can aim ultrasonic waves toward a location at which drug-containing infusate 154 exits the catheter 102. The focused ultrasound can enhance dispersion of the drug, and/or control the direction and degree to which the drug disperses. Focused ultrasound can be used to coordinate delivery with a physiological parameter of the patient, such as natural CSF flow. Focused ultrasound can also be used to enhance or direct drug distribution without pulsatile delivery.

Figure 17:
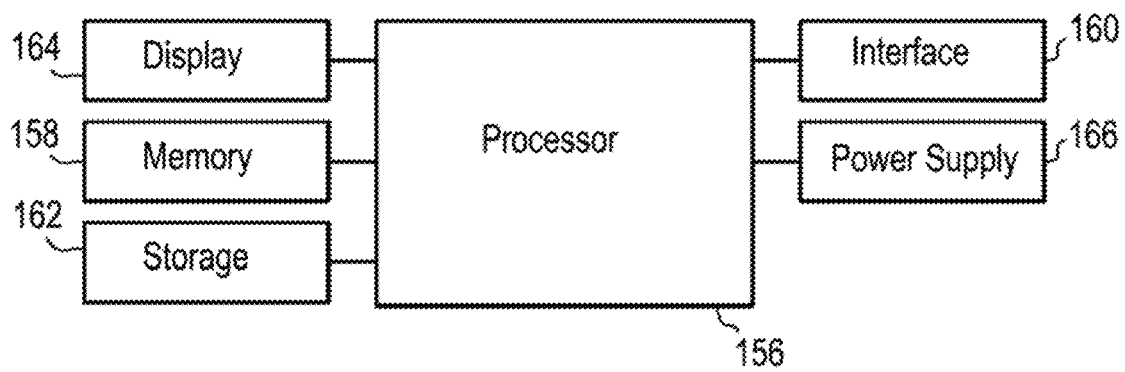
FIG. 17 is a schematic hardware diagram of a controller of the system of FIG. 1.

FIG. 17 illustrates a block diagram of the physical components of an exemplary embodiment of the controller 104. Although an exemplary controller 104 is depicted and described herein, it will be appreciated that this is for sake of generality and convenience. In other embodiments, the controller 104 may differ in architecture and operation from that shown and described here. The controller 104 can be a tablet computer, mobile device, smart phone, laptop computer, desktop computer, cloud-based computer, server computer, and so forth. One or more portions of the controller 104 can be implanted in the patient. Delivery control software can execute on the controller 104. The software can execute on a local hardware component (e.g., a tablet computer, smart phone, laptop computer, or the like) or can execute remotely (e.g., on a server or cloud-connected computing device in communications coupling with the controller).

The illustrated controller 104 includes a processor 156 which controls the operation of the controller 104, for example by executing embedded software, operating systems, device drivers, application programs, and so forth. The processor 156 can include any type of microprocessor or central processing unit (CPU), including programmable general-purpose or special-purpose processors and/or any of a variety of proprietary or commercially-available single or multi-processor systems. As used herein, the term processor can refer to microprocessors, microcontrollers, ASICs, FPGAs, PICs, processors that read and interpret program instructions from internal or external memory or registers, and so forth. The controller 104 also includes a memory 158, which provides temporary or permanent storage for code to be executed by the processor 156 or for data that is processed by the processor. The memory 158 can include read-only memory (ROM), flash memory, one or more varieties of random access memory (RAM), and/or a combination of memory technologies. The various components of the controller 104 can be interconnected via any one or more separate traces, physical busses, communication lines, etc.

The controller 104 can also include an interface 160, such as a communication interface or an I/O interface. A communication interface can enable the controller 104 to communicate with remote devices (e.g., other controllers or computer systems) over a network or communications bus (e.g., a universal serial bus). An I/O interface can facilitate communication between one or more input devices, one or more output devices, and the various other components of the controller 104. Exemplary input devices include touch screens, mechanical buttons, keyboards, and pointing devices. The controller 104 can also include a storage device 162, which can include any conventional medium for storing data in a non-volatile and/or non-transient manner. The storage device 162 can thus hold data and/or instructions in a persistent state (i.e., the value is retained despite interruption of power to the controller 104). The storage device 162 can include one or more hard disk drives, flash drives, USB drives, optical drives, various media disks or cards, and/or any combination thereof and can be directly connected to the other components of the controller 104 or remotely connected thereto, such as through the communication interface. The controller 104 can also include a display 164, and can generate images to be displayed thereon. In some embodiments, the display 164 can be a vacuum fluorescent display (VFD), an organic light-emitting diode (OLED) display, or a liquid crystal display (LCD). The controller 104 can also include a power supply 166 and appropriate regulating and conditioning circuitry. Exemplary power supplies include batteries, such as polymer lithium ion batteries, or adapters for coupling the controller 104 to a DC or AC power source (e.g., a USB adapter or a wall adapter).

Figure 18:
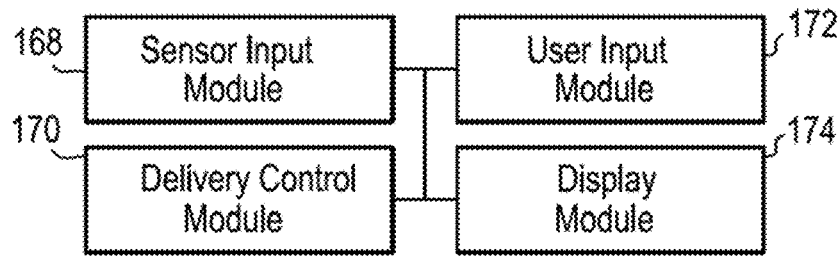
FIG. 18 is a functional block diagram of the controller of FIG. 17.

The various functions performed by the controller 104 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the controller can include fewer or more modules than what is shown and described herein. FIG. 18 is a schematic diagram of the modules of one exemplary embodiment of the controller 104.

As shown in FIG. 18, the controller 104 can include a sensor input module 168 configured to receive information from the sensor(s) 108. The sensor input module 168 can read and interpret output signals supplied from the sensors 108 to the processor 156, e.g., via a general purpose input/output pin of the processor. The sensor input module 168 can optionally perform various processing on the sensor signals, such as frequency detection, phase detection, debouncing, analog-to-digital conversion, filtering, and so forth.

The controller 104 can also include a delivery control module 170 configured to control the pump or actuator 106 to infuse or aspirate fluid from the patient and/or to control the catheter 102 (e.g., an auger, piston, transducer, ultrasound system, etc.). For example, when an "infuse" instruction is issued, the delivery control module 170 can cause power to be supplied to the pump 106 to begin pumping infusate through the catheter 102, or cause an electronically-actuated valve to open such that infusate stored under pressure is placed in fluid communication with the catheter and flows therethrough. In some embodiments, the delivery control module 170 can be configured to cut off power to the pump 106 or to close a valve when a pressure sensor indicates that the pressure in the system has reached a predetermined threshold amount. When an "aspirate" instruction is issued, the delivery control module 170 can cause power to be supplied to the pump 106 to begin pumping fluid out of the catheter 102.

The controller 104 can include a user input module 172 configured to receive one or more user inputs, e.g., as supplied by a user via the interface 160. Exemplary user inputs can include infusion parameters, patient information, treatment protocols, and so forth, as discussed further below.

The controller 104 can also include a display module 174 configured to display various information to the user on the display 164, such as a graphical or textual user interface, menus, buttons, instructions, and other interface elements. The display module 174 can also be configured to display instructions, warnings, errors, measurements, and calculations.

Figure 19:
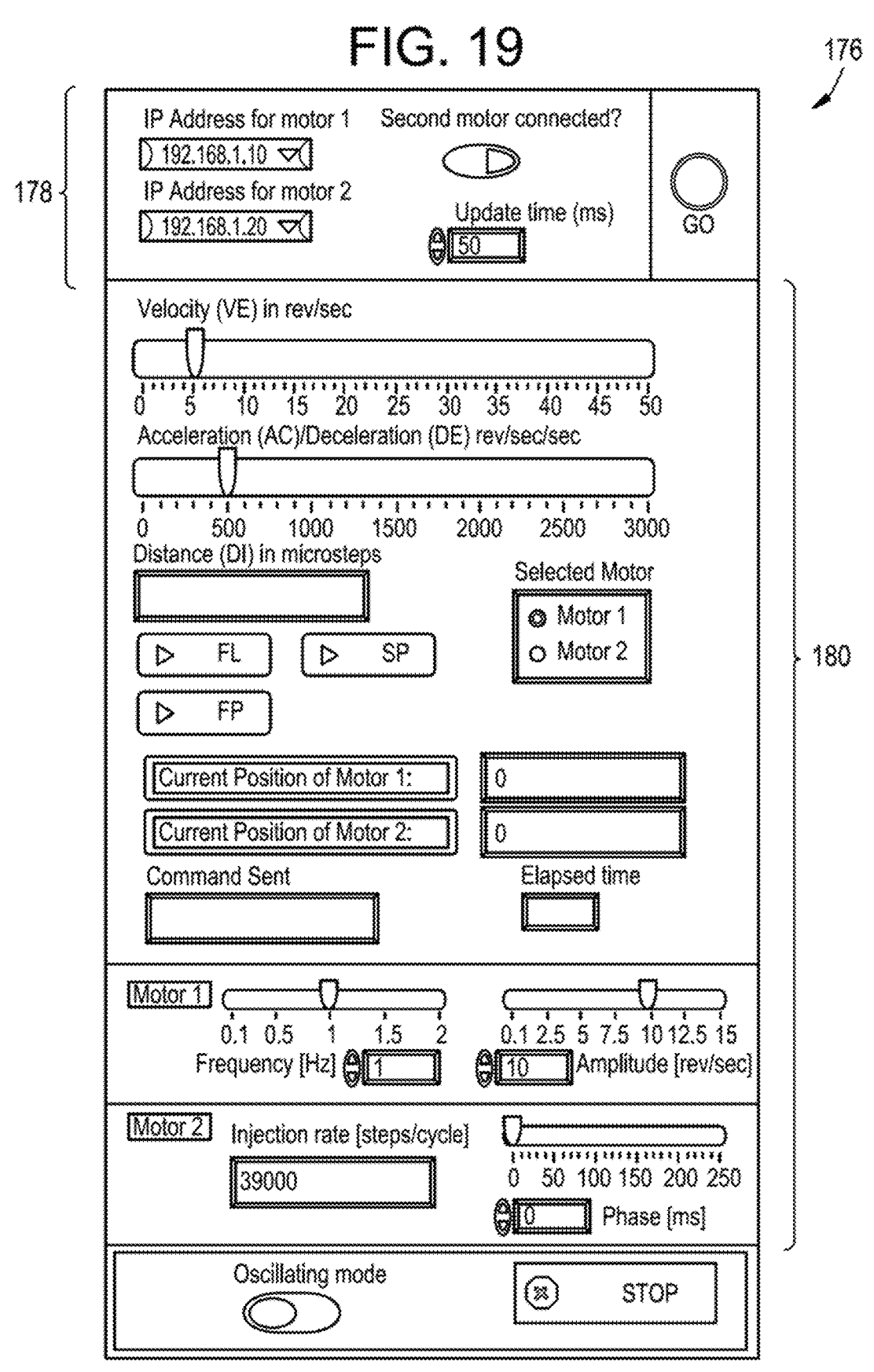

FIG. 19 illustrates an exemplary graphical user interface 176 that can be displayed to the user by the display module 174 and through which a user can supply information to the user input module 172. The illustrated interface 176 is configured for use with a pump system 106 that includes first and second motors or linear actuators that can be operated to apply a force to respective syringe pumps for delivering infusate to the catheter 102 and for withdrawing or aspirating fluid from the catheter.

The user interface 176 can include a motor communication panel 178 for displaying various information associated with the motors. This information can include the connection status of the motors, an IP or other software address of the motors, and a motor communication frequency or update time. The user can interact with the motor communication panel 178 to select or change the motor addresses and the update time.

The user interface 176 can include a motor setting panel 180 for adjusting various motor settings and for displaying the current setting to the user. The motor setting panel 180 can include controls for the motor velocity, motor acceleration, distance of syringe movement as a function of motor steps, current motor positions, infusion frequency, infusion amplitude, infusion rate, infusion phase, and so forth.

The controller 104 can be configured to control various infusion and/or aspiration parameters to achieve customized delivery. This can allow the delivery to be tailored based on the therapeutic application. Exemplary parameters that can be controlled by the controller 104 include infusion type, infusion rate, infusion volume, time between infusions, oscillatory rate, infusion and withdraw ratio, infusion phase timing, aspiration type, aspiration rate, time between aspirations, aspiration volume, and so forth.

The pump or actuator system 106 can be configured to supply a drug or a drug-containing fluid to the catheter 102 and/or to aspirate fluid from the catheter. The system 106 can include one or more pumps. For example, the system 106 can include a plurality of pumps, each being associated with and in fluid communication with a corresponding lumen of the catheter 102. The pumps can also be associated with and in fluid communication with respective reservoirs for holding a volume of fluid. In some embodiments, the system 106 can include first and second syringe pumps coupled to electronic linear actuators configured to advance or retract the plungers of the syringe pumps in response to control signals received from the controller 104. In some embodiments, the system 106 can include a peristaltic pump, an auger pump, a gear pump, a piston pump, a bladder pump, etc. One or more portions of the system 106 can be implanted in the patient. The system 106 can include any of a variety of implantable or extracorporeal pumps. In some embodiments, the system 106 can include a fully-implanted, programmable pump and a fully-implanted fluid reservoir containing fluid to be delivered using the system. In some embodiments, the entire system 106 can be implantable, e.g., to facilitate chronic treatment methods.

The sensor 108 can be a single sensor or a plurality of sensors. Exemplary sensors include pressure sensors, electrocardiogram sensors, heart rate sensors, temperature sensors, PH sensors, respiration rate sensors, respiration volume sensors, lung capacity sensors, chest expansion and contraction sensors, intrathoracic pressure sensors, intraabdominal pressure sensors, and the like. One or more of the sensors 108 can be implanted in the patient. One or more of the sensors 108 can be mounted on, inserted through, or formed in or on the catheter 102. The sensors 108 can also be remote from the catheter 102. In some embodiments, the sensors 108 can include a pressure sensor disposed in or on the catheter 102 for measuring CSF pressure adjacent to the catheter and an ECG sensor for measuring the patient's heart rate. The sensors 108 can be connected (via wires or via a wireless connection) to the sensor input module 168 of the controller 104.

As noted above, one or more components of the delivery system 100 and, in some embodiments, all components of the delivery system, can be implanted in the patient. Implanting some or all of the delivery system 100 can facilitate chronic or long-term drug delivery (e.g., over a period of days, weeks, months, or years) via non-invasive or outpatient procedures.

Figure 20A:
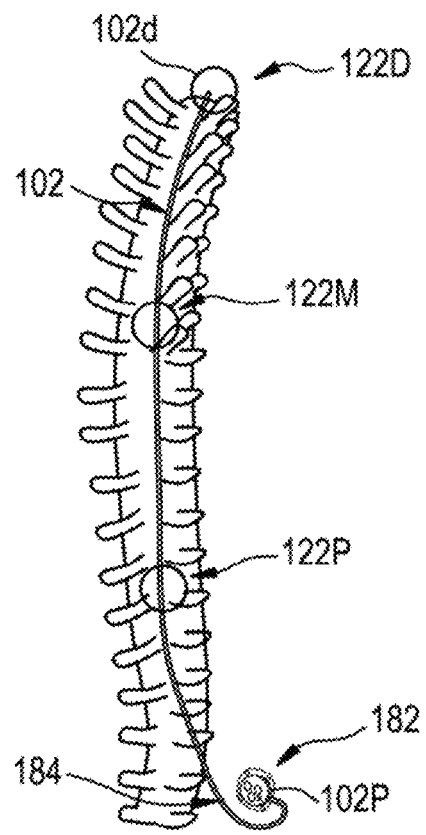
FIG. 20A is a perspective view of a catheter of the system of FIG. 1 implanted in a patient and shown with an infusion port.
Figure 20B:
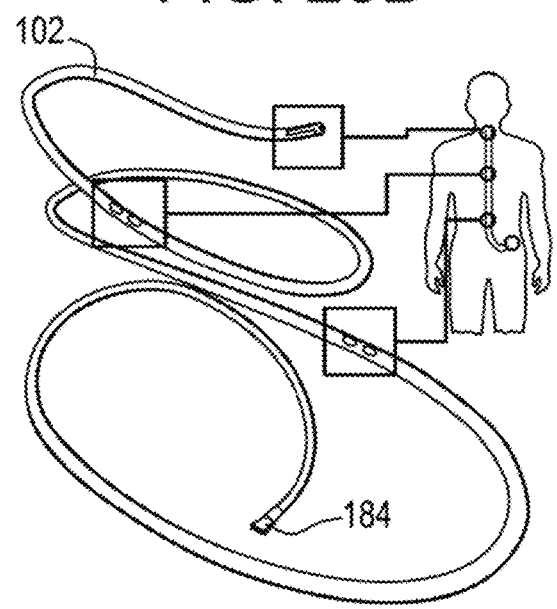
FIG. 20B is a perspective schematic view of the catheter and patient of FIG. 20A.
Figure 20C:
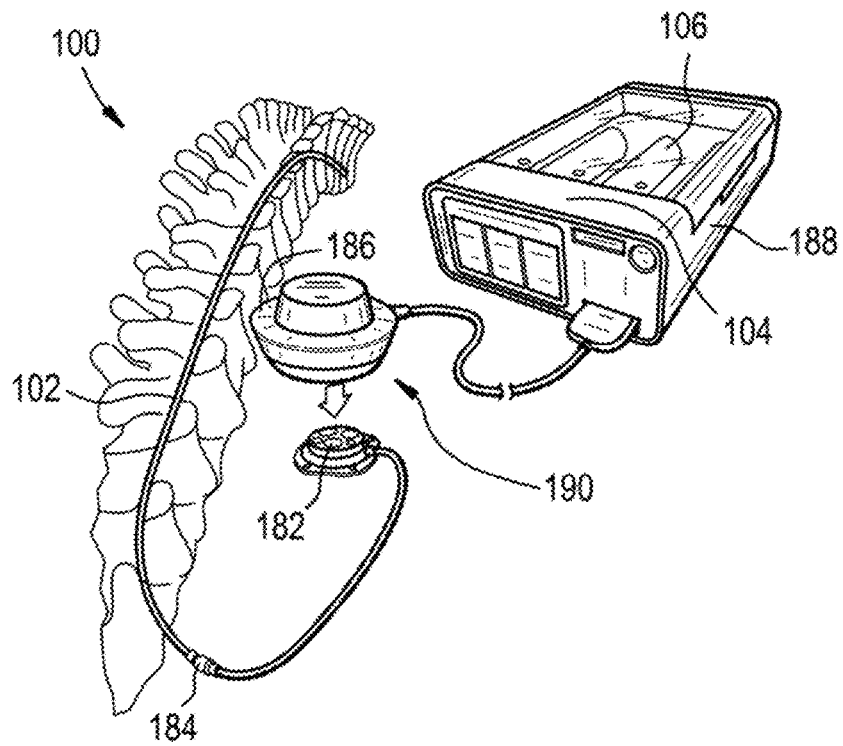
FIG. 20C is a perspective view of the catheter and patient of FIG. 20A, shown with an infusion port, an injector, and a controller.

FIGS. 20A-20B illustrate the catheter 102 fully-implanted in a patient. As shown, the catheter 102 can be configured for positioning within a patient's intrathecal space and can extend substantially the entire length of the spinal column or along any portion thereof. The catheter 102 can include one or more fluid lumens. The catheter 102 can also include one or more fluid ports. In some embodiments, the catheter 102 can include a plurality of fluid lumens, with each of the plurality of fluid lumens having its own respective fluid port. In the illustrated embodiment, the catheter 102 includes three fluid lumens and three respective fluid ports 122P, 122M, and 122D. The catheter 102 can also include one or more sensors 108 (e.g., pressure sensors). In the illustrated embodiment, each of the fluid ports 122P, 122M, 122D includes a sensor 108P, 108M, 108D mounted adjacent or in proximity thereto. A proximal end of the catheter 102 can be coupled to a fully implanted, transcutanous, or extracorporeal infusion port 182 through which fluid can be delivered to (or removed from) the various lumens of the catheter and through which one or more sensors 108 on the catheter can be coupled to a controller 104 or other device. A quick-connector system 184 can be used to couple the catheter 102 to the infusion port 182. The micro-connector 184 can include air and/or bacterial filters and can be a zero-dead-volume connector. The pump 106 and the controller 104 can be mounted together in a chassis or housing 188, as shown in FIG. 20C, which can be coupled to an injector 190 configured to mate with the infusion port 182. The injector 190 can include magnetic alignment features 186 for ensuring that the injector is properly aligned with respect to a subcutaneous infusion port 182.

Figure 20D:
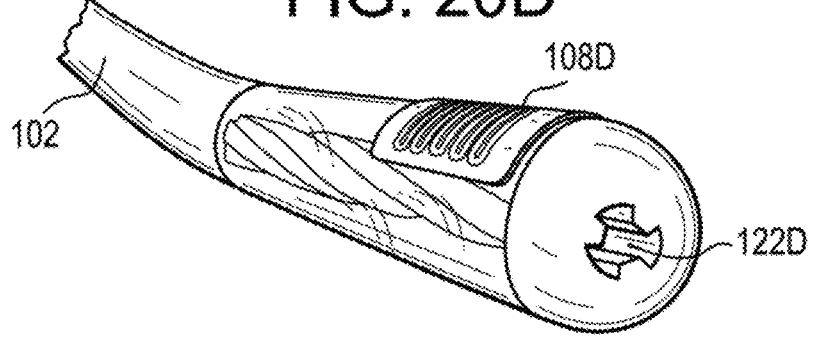
FIG. 20D is a perspective view of a distal fluid port of the catheter of FIG. 20A.
Figure 20E:
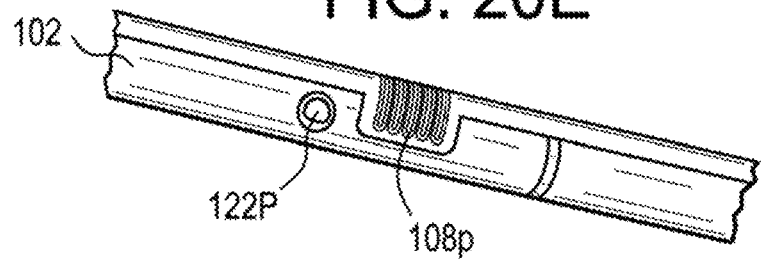
FIG. 20E is a perspective view of a middle or proximal fluid port of the catheter of FIG. 20A.

As shown in FIG. 20D, the distal or cranial/cervical tip of the catheter 102 can have a modified shape to encourage turbulent flow therethrough (e.g., a helical or corkscrew shaped lumen or fluid port 122D as described above). Any of a variety of other shapes can be used. The other ports 122M, 122P can be similarly configured, can have a simple circular cross-section as shown in FIG. 20E, or can have any other configuration described herein.

The system 100 illustrated in FIGS. 20A-20E can be used in acute and/or chronic applications in any of a variety of ways.

For example, the catheter 102 can be used to deliver three different drugs (e.g., one drug through each different lumen of the catheter).

By way of further example, the catheter 102 can be used for localized delivery of different drugs to different areas of the spine.

As yet another example, the catheter 102 can be used to deliver the same drug with substantially instantaneous distribution along the entire spinal column.

In another example, one port of the catheter 102 can be used to aspirate while another is used to infuse in order to draw the infused fluid through the spinal canal. In some embodiments, fluid can be infused through a lower-lumbar port 122P and fluid can be aspirated through a cervical port 122D to "pull" the infused fluid up the spinal column.

In another example, fluid can be infused through a port 122D disposed in the cervical region of the patient's spine to propel infused drug into the cranial space.

By way of further example, the catheter 102 can be used to substantially contain an infused drug to a given area of the spine. In some embodiments, fluid can be infused through a lower-lumbar port 122P and fluid can be withdrawn from a mid-lumbar port 122M to keep the infused drug between the two ports 122P, 122M in the lumbar region of the patient's spine.

In an exemplary method, infusions and aspirations via multiple lumens and ports can be staged or combined in a sequence to create and advance a significant bolus at improved, controlled, and convenient rates. The method can include simultaneous aspiration/infusion between deliberately spaced ports. The delivery can be enhanced by a preparation step of removing a safe amount of CSF to be replaced in later procedure steps when advancing the bolus. The method can include a final stage of synchronized pulsatile infusion. The method can allow a large bolus to be formed more quickly, can allow controlled dosing, and/or can allow the bolus to be delivered closer to the brain or other target site. The method can be performed using a catheter that tapers from the proximal end towards the distal end. A tapered catheter profile in which the catheter diameter reduces distal of each port can enable the catheter to be longer, be easier to introduce/navigate, and have device reach significantly closer to the target site. Port designs and locations can be optimized based on dose and other factors. The catheter can be placed such that fluid exiting the ports flows against patient anatomy (e.g., a blind lumen end, lumen sidewall, or lumen constriction) to promote turbulent flow of the infusate upon exiting the catheter. In an initial step, a volume of patient CSF can be aspirated through one or more ports of the catheter. In an exemplary embodiment, about 10% by volume of the patient's CSF can be aspirated through the catheter and stored in a reservoir. The amount of CSF that is aspirated can be based on a clinically-determined safe level. In a subsequent delivery step, CSF can be aspirated from the patient through a distal fluid port 122D of the catheter 102 while a drug is simultaneously infused into the patient through a middle port 122M of the catheter. This can cause a bolus of drug to form between the middle and distal ports 122M, 122D. The ports can be located along the length of the catheter to define the bolus size or dose. In an advancement step, the bolus of drug can be advanced within the patient. This can be achieved by infusing previously-aspirated CSF from the reservoir into the patient through a proximal port 122P of the catheter 102. This infusion can urge the bolus distally towards the target site and can continue until normal or safe CSF pressure is reached within the patient. While previously-aspirated CSF is used to advance the bolus in the above example, other fluid can be used instead or in addition, such as drug-containing fluid. Before, during, or after advancement of the bolus, infusion of CSF and/or drug-containing fluid can be performed in a pulsatile manner in coordination with one or more physiological parameters of the patient. The above method can also be performed using only a proximal port 122P and a distal port 122D. The proximal, middle, and distal ports 122P, 122M, 122D can be spaced along the length of the spinal column as shown in FIG. 20A, or can all be contained in a discrete region of the spine (e.g., the cervical spine, the thoracic spine, the lumbar spine, etc.).

The systems disclosed herein can be used in any of a variety of drug delivery methods.

In an exemplary method, the infusion pump 106 can be configured to pump a drug or a drug-containing fluid through the catheter 102 and into a patient (e.g., into an intrathecal space of the patient). The catheter 102 can be inserted into the patient at any of a variety of locations. For example, a percutaneous puncture can be formed in the patient using a needle. The puncture can be formed in the lumbar region of the spine, or in any other region of the spine, e.g., the cervical region between C1 and C2. The needle can have a bent distal tip that helps steer the catheter 102 to be parallel to the spinal cord. The catheter 102 can be inserted through the needle and guided through the intrathecal space along the spinal cord. The infusion can be performed in proximity to the percutaneous puncture, or the catheter 102 can be advanced some distance within the patient. In some embodiments, the catheter 102 can be inserted in the lumbar spine and advanced to the cervical spine or to the cisterna magna. Infusion can be performed at any point along the length of the catheter 102. Fluid can be infused from a distal end of the catheter 102 (e.g., in a cervical region of the spine), the catheter can be withdrawn proximally, and further infusion can be performed at a more caudal location (e.g., in a lumbar region of the spine).

The pump 106 can be controlled by the controller 104 to synchronize or otherwise coordinate delivery of the drug with the patient's natural CSF flow or pulsation, or with other physiological parameters of the patient (e.g., heart rate, respiration rate, lung capacity, chest expansion and contraction, intrathoracic pressure, intraabdominal pressure, etc.). The infusion profile can be tailored to override the natural CSF pulsation to drive the infusate to a target site. Alternatively, or in addition, the infusion profile can be tailored to coordinate with and leverage the natural CSF pulsation to move the infusate towards the target site.

Figure 21A:
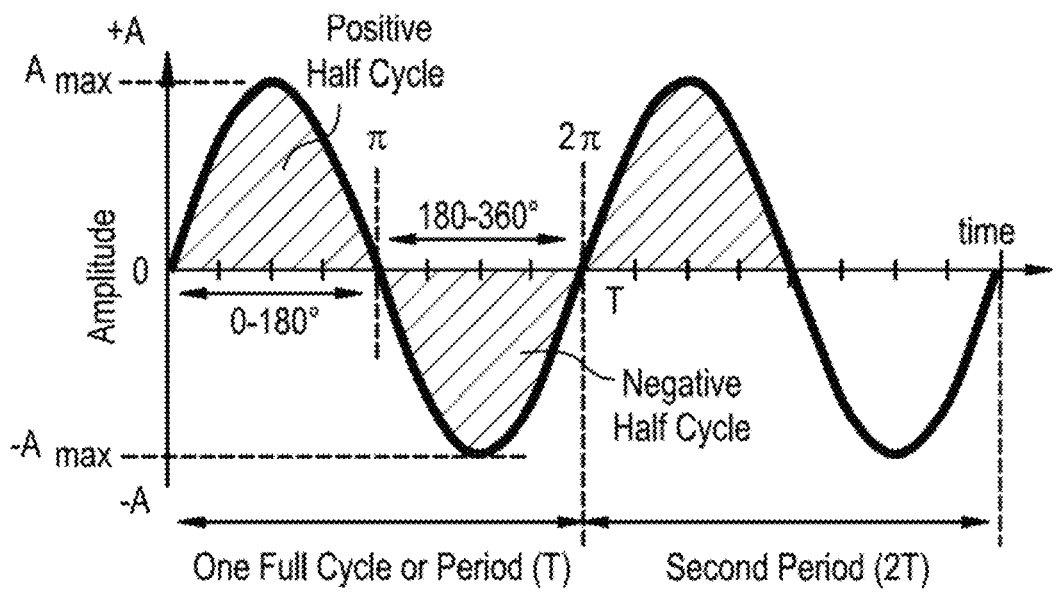
FIG. 21A is a diagram illustrating the controller of the system of FIG. 1 coordinating control of a pump with a sensed physiological parameter.
Figure 21A:
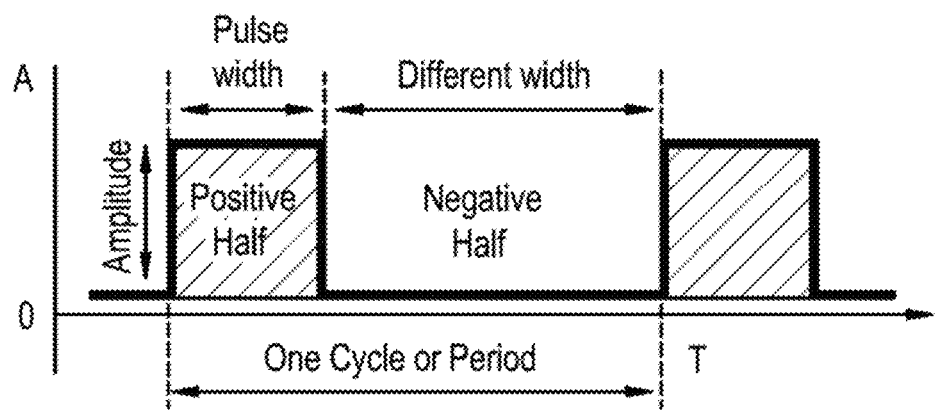

Readings from a pressure sensor 108 can be received by the controller 104, which can perform signal processing on the sensor output to determine various characteristics of the patient's CSF flow (e.g., phase, rate, magnitude, etc.). The controller 104 can then control the pump 106 based on these measured characteristics to deliver a drug in coordination with the natural CSF flow, optionally synchronizing the delivery in real time. For example, as shown in the upper portion of FIG. 21A, the controller 104 can convert the measured pulsatile flow of the CSF into a sinusoidal approximation. The controller 104 can then output a pump control signal, as shown in the lower portion of FIG. 21A, to drive the infusion pump 106 in coordination with the CSF pulsation.

In some instances, the pressure sensed by the pressure sensor 108 can be influenced by the infusion through the catheter 102. Accordingly, it can be desirable to have another way of detecting or estimating CSF flow. Thus, in some embodiments, the system 100 can be operated initially in a "learning" mode in which no infusion takes place and the controller 104 establishes a correlation between CSF pulsation and heart rate (e.g., as detected by an ECG sensor 108 in communications coupling with the controller). In general, CSF pulsation tracks heart rate with a slight delay. Once a correlation is established, the system 100 can be operated in an "infusion" mode in which infusate is delivered through the catheter 102 and the CSF pulsation is detected or estimated based on measured heart rate (instead of or in addition to detecting or estimating the CSF pulsation based on the pressure sensor 108 output). In other words, the system 100 can interpolate or estimate the CSF flow based on the ECG output, without necessarily having to rely on the pressure sensor output. This can allow the pressure sensor to be used for other purposes, such as monitoring the infusion pressure to allow the controller 104 to automatically regulate delivery to a target pressure or pressure range.

In one example use of the systems described herein, a drug can be delivered to the intrathecal space via a simple bolus injection (a fast infusion of a volume of fluid) which then just diffuses slowly along the spinal column.

In another example, a bolus injection can be performed to deliver the drug and then the system can be used to create a pulsation behind the bolus by changing oscillation rate/pulsation rate to override the natural CSF pulse and make the bolus move more quickly towards a target location (e.g., the brain). The pulsation can be created by repeatedly withdrawing or aspirating a volume of CSF and then pumping that same volume back into the patient to create a pulse.

In another example, infusion of the drug itself can be used to create a pulsation effect to urge the drug along the intrathecal space. In this example, a first volume of the drug can be infused (e.g., 0.1 ml) and then a second, smaller volume can be withdrawn (e.g., 0.05 ml). This can be repeated to create a pulse with a net infusion on each cycle. The process can be repeated until the desired dose is delivered. While an infusion-to-withdrawal ratio of 2:1 is discussed above, it will be appreciated that any ratio can be used. In addition, the rate of infusion and withdrawal can be controlled (e.g., by infusing quickly and withdrawing slowly) to create a burst of fluid towards a target location (e.g., the top of the spinal column).

In the devices and methods disclosed herein, infusion and/or aspiration can be coordinated with one or more physiological parameters of a patient (e.g., natural CSF flow, heart rate, respiration rate, etc.).

Figure 21B:
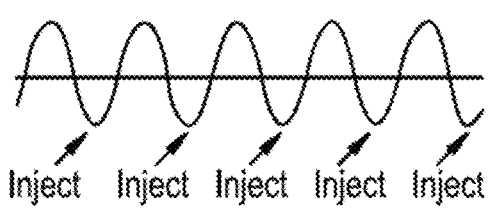
FIG. 21B is a diagram illustrating use of the system of FIG. 1 to synchronize delivery of a drug with an ascending wave of the patient's natural CSF pulsation.
Figure 21C:
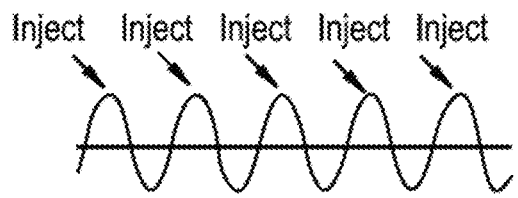
FIG. 21C is a diagram illustrating use of the system of FIG. 1 to synchronize delivery of a drug with a descending wave of the patient's natural CSF pulsation.

The direction of drug distribution at an intrathecal target site can be controlled at least to some degree based on the timing at which the drug is delivered relative to the timing of the CSF flow. For example, infusion that is synchronized with the ascending wave of CSF flow, as shown in FIG. 21B, can be distributed to a greater degree in the cranial direction whereas infusion that is synchronized with the descending wave of CSF flow, as shown in FIG. 21C, can be distributed to a greater degree in the caudal direction of the spinal canal.

In some embodiments, a dual- or multi-lumen catheter can be used for alternating, repetitive infusion and aspiration, which can further enhance drug distribution.

The systems and methods disclosed herein can provide an improved means for delivering a drug to the intrathecal space, as compared with traditional lumbar bolus injections which do not reach the remote portions of the spinal canal or brain efficiently (if at all).

While intrathecal delivery is generally described in the examples given above, it will be appreciated that the systems and methods herein can be used in other applications, with appropriate modification of size or other parameters as will be appreciated by those having ordinary skill in the art. For example, the systems and methods disclosed herein can be used for intrarterial or intravenous delivery. Such systems and methods can include infusion and/or aspiration that is coordinated with one or more physiological parameters of a patient (e.g., natural CSF flow, heart rate, respiration rate, etc.).

In some embodiments, the drug can be delivered in a non-pulsatile manner and/or without necessarily coordinating the delivery with a physiological parameter of the patient. For example, alternating or otherwise-coordinated aspiration and infusion can be used to deliver the drug to a target site. By way of further example, the drug can be infused and then a buffer can be infused behind the drug to enhance distribution or to move the drug towards a target site.

An exemplary method can include inserting at least a portion of a catheter into a patient and delivering a drug to a target region of the patient. At least a portion of the catheter can be disposed in the target region. The drug can be delivered in a pulsatile manner. The drug can be delivered in coordination with a physiological parameter of the patient (e.g., the patient's natural CSF flow and/or the patient's heart rate).

The target region can be an intrathecal space of the patient. The target region can be a subpial region of the patient (e.g., a subpial region of the spinal cord and/or a subpial region of the brain). The target region can be a cerebellum of the patient. The target region can be a dentate nucleus of the patient. The target region can be a dorsal root ganglion of the patient. The target region can be a motor neuron of the patient. The drug can include an antisense oligonucleotide. The drug can include a stereopure nucleic acid. The drug can include a virus. The drug can include adeno-associated virus (AAV). The drug can include a non-viral gene therapy. The drug can include vexosomes. The drug can include liposomes. The method can include performing gene therapy by delivering the drug (e.g., by delivering a virus such as AAV). The method can include performing gene editing by delivering the drug (e.g., by delivering a virus such as AAV). The method can include performing gene switching by delivering the drug (e.g., by delivering a virus such as AAV). The method can include performing non-viral gene therapy by delivering the drug (e.g., by delivering vexosomes and/or liposomes).

In some embodiments, the method can include determining a total CSF volume of the patient and tailoring the delivery based on the total CSF volume. For example, MRI or other imaging techniques, with or without contrast, can be used to assess the overall CSF volume of the patient. The delivery of the drug can then be tailored based on the measured volume. For example, a larger volume of buffer can be used with patients having a greater total CSF volume and a smaller volume of buffer can be used with patients having a lesser total CSF volume. By way of further example, infusion amplitude, infusion velocity, aspiration volume, aspiration amplitude, and other parameters can be varied in accordance with the measured total CSF volume.

The infusion volume can range from about 0.05 mL and about 50 mL. The infusion rate can range from about 0.5 mL/min to about 50 mL/min.

The following are exemplary drug delivery methods that can be performed using the systems disclosed herein:

Example A

Alternating Pulsatile infusions of Drug (Pump 1) and Buffer/Saline (Pump 2)
Drug Total Volume: 2.2 mL
Buffer Total Volume: 4.4 mL
Infusion rate for both pumps: 15 mL/min
Cycles: 10 cycles at lumbar then 10 cycles at Cisterna magna
Time between cycles: 100 milliseconds
Infusion description: At lumbar section Pump 1 infuses 0.11 mL at 15 mL/min, a 100 ms pause, Pump 2 infuses 0.22 mL at 15 mL/min, a 100 ms pause (cycle 1). This is repeated for a total of 10 cycles at the lumbar. Catheter is threaded up to the cisterna magna. Pump 1 infuses 0.11 mL at 15 mL/min, a 100 ms pause, Pump 2 infuses 0.22 mL at 15 mL/min, a 100 ms pause (cycle 1). This is repeated for a total of 10 cycles at the cisterna magna.

Example B

Alternating Pulsatile infusions of Drug (Pump 1) and Buffer/Saline (Pump 2)
Drug Total Volume: 3 mL
Buffer Total Volume: 20 mL
Infusion rate for both pumps: 4 mL/min
Cycles: 13 cycles at thoracic region
Time between alternating pump 1 to pump 2: 1000 milliseconds
Time between cycles (pump 2 to pump 1): 5000 milliseconds
Infusion description: At lumbar section Pump 1 infuses 0.231 mL at 4 mL/min, a 1000 ms pause, Pump 2 infuses 2.0 mL at 4 mL/min, a 5000 ms pause (cycle 1). This is repeated for a total of 13 cycles at the thoracic region.

Example C

Alternating Pulsatile infusions of Drug (Pump 1) and Buffer/Saline (Pump 2)
Drug Total Volume: 5 mL
Buffer Total Volume: 8 mL
Infusion rate for pump 1: 37 mL/min
Infusion rate for pump 2: 20 mL/min
Cycles: 5 cycles at thoracic region
Time between cycles: 10 milliseconds
Infusion description: At lumbar section Pump 1 infuses 1 mL at 37 mL/min, a 10 ms pause, Pump 2 infuses 1.6 mL at 30 mL/min, a 100 ms pause (cycle 1). This is repeated for a total of 5 cycles at the thoracic region.

Figure 22:
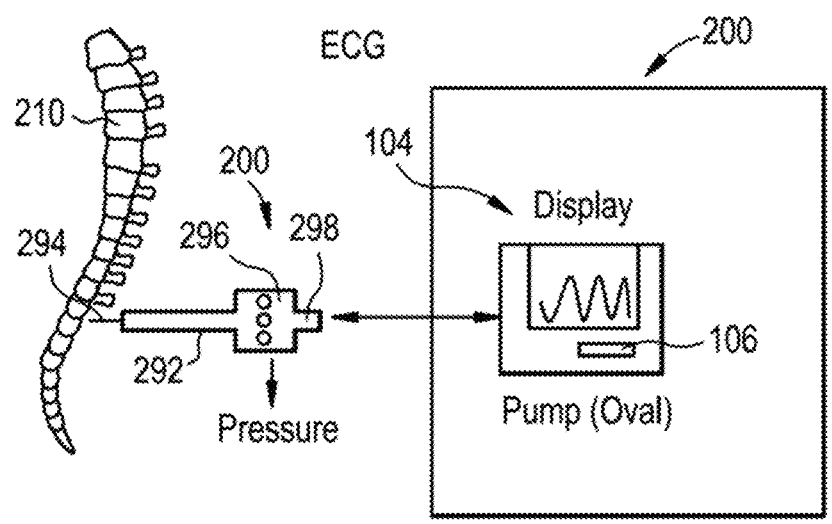
FIG. 22 is a schematic diagram of a drug delivery system with a smart lumbar puncture needle.

FIG. 22 illustrates a drug delivery system 200 that includes a lumbar puncture needle 292. The needle 292 can include a sensor 294 (e.g., a pressure sensor) mounted adjacent a distal tip of the needle. Accordingly, upon insertion of the needle 292 into the patient 210, the sensor 294 can measure the pressure or other properties of the patient's CSF. The needle 292 can also include an integrated or remote display 296 for displaying the output of the sensor 294 to a user. In some embodiments, the display 296 can be mounted along the length of the needle 292, distal to a proximal Luer or other connector 298 of the needle. The needle body 292 can be a tubular metal shaft with a sharpened or angled tip. Fluid tubing can be coupled to the needle 292, e.g., via a proximal connector 298, and to a programmable pump 106. A controller 104 of the type described above can be programmed to control the pump 106 to deliver fluid through the needle 292, e.g., in a pulsatile fashion in coordination with a physiological parameter of the patient. The needle 292 can be used to deliver a drug, to deliver a buffer, and/or to aspirate fluid. In some embodiments, a catheter 102 of the type described above can be inserted through the needle 292 and the fluid delivery or aspiration can be performed through the catheter.

Figure 23:
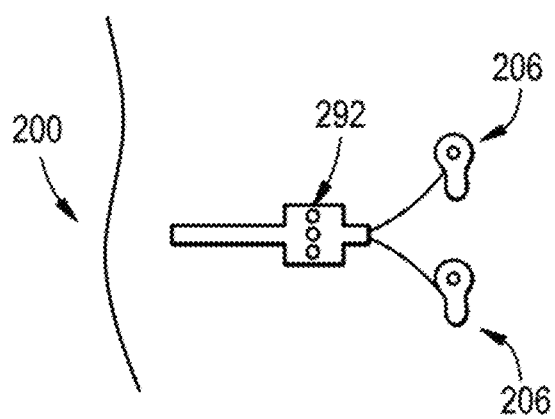
FIG. 23 is a schematic diagram of a drug delivery system with manual pumps.

As shown in FIG. 23, a manual pump 206 can be provided instead of or in addition to the programmable pump 106 and controller 104 shown in FIG. 22. As shown, a first fluid lumen of the needle 292 (or of a catheter 102 inserted through the needle) can be coupled to a first pump 206A that includes a first reservoir and a first flush dome. Similarly, a second fluid lumen of the needle 292 (or of a catheter 102 inserted through the needle) can be coupled to a second pump 206B that includes a second reservoir and a second flush dome. A user can exert manual finger pressure on the first and second flush domes to selectively press fluid contained in the first and second reservoirs into the patient. Accordingly, the user's manual actuation rate and actuation pressure can dictate the infusion frequency and volume. A user can thus pulse the delivery manually. The flush domes can be configured such that each successive actuation of the dome delivers a fixed and predetermined volume of fluid. For example, each push of the flush dome can be configured to deliver 0.1 ml of fluid. In some embodiments, one of the reservoirs can be filled with a buffer solution and the other reservoir can be filled with a drug-containing solution.

FIGS. 24A-24G illustrate a drug delivery system 300 that can include a needle 302 and a catheter 304 insertable through the needle. The needle 302 can be a lumbar puncture needle. The catheter 304 can be a single lumen catheter or a multi-lumen catheter. For example, a dual-lumen catheter that bifurcates at a proximal portion of the catheter can be used as shown. Fluid tubing 306 can be coupled to the catheter 304, e.g., via one or more proximal connectors 308, and to a programmable pump system 310. The needle 302 or catheter 304 can also be connected directly to the pump system 310.

In some embodiments, the pump system 310 can include first and second pumps configured to infuse and/or aspirate fluid through respective lumens of the catheter 304. Any of a variety of pumps can be used, including a linear-actuator syringe pump of the type shown in FIG. 24A. A controller 104 of the type described above can be programmed to control the pump system 310 to deliver fluid through the catheter 304, e.g., in a pulsatile fashion in coordination with a physiological parameter of the patient. The catheter 304 can be used to deliver a drug, to deliver a buffer or other fluid, and/or to aspirate fluid. In some embodiments, the catheter 304 can be omitted and fluid can be infused through the needle 302 directly and/or aspirated through the needle directly. One or more of the fluid connections can be made with the needle 302 instead of or in addition to the catheter 304. For example, the fluid tubing through which a drug is to be delivered can be coupled directly to the catheter 304 to deliver the drug through the catheter and fluid tubing through which a buffer, chaser, or other fluid is to be delivered can be coupled directly to the needle 302 to deliver the fluid through the needle.

The needle 302 can be defined by a hollow tubular body configured to receive a catheter and/or fluid therethrough. The needle 302 can be a lumbar puncture needle sized and configured for insertion into the intrathecal space through a lumbar insertion point. The needle 302 can have a curved distal tip configured to naturally steer the needle into the intrathecal space as the needle is inserted into the patient in the lumbar region of the spine. An opening can be formed in the distal end of the needle 302 through which an inserted catheter 304 can extend.

Figure 24A:
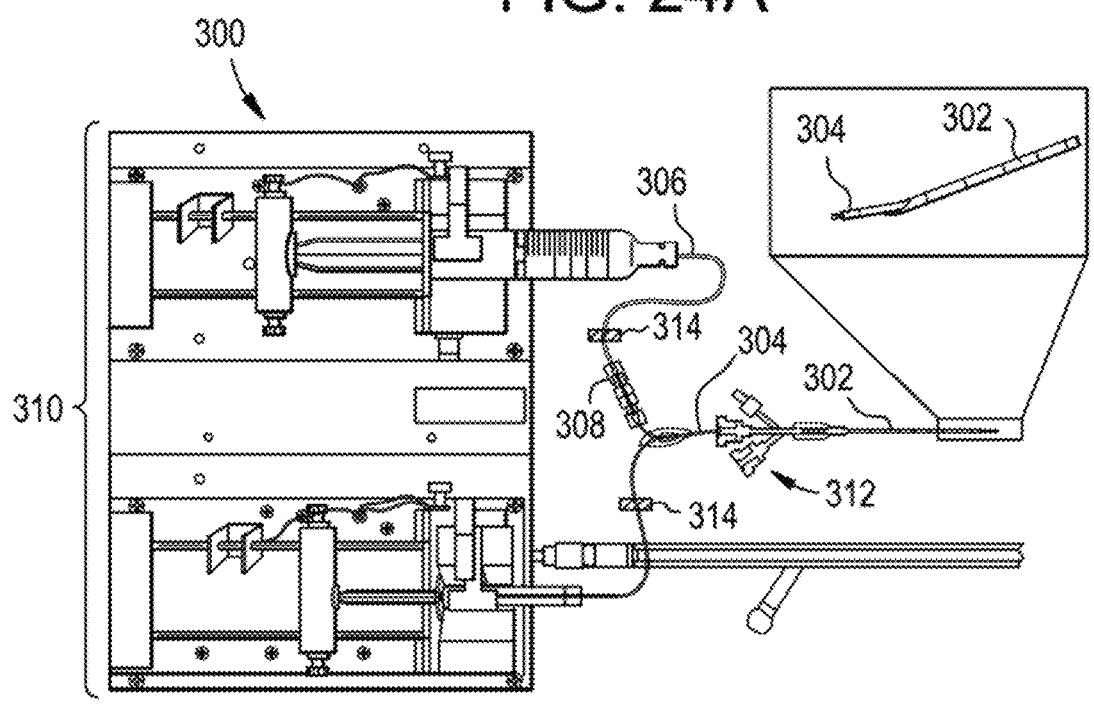
FIG. 24A is a schematic view of a drug delivery system.
Figure 24B:
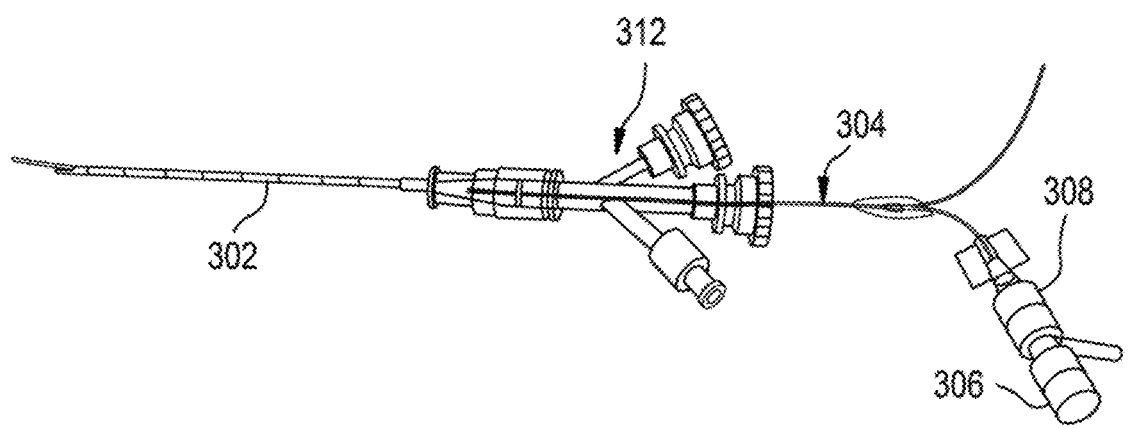
FIG. 24B is a perspective view of a needle, hub, and catheter of the system of FIG. 24A.

The proximal end of the needle can be coupled to a fluid hub 312. As shown in FIG. 24B, the hub 312 can be a "W" hub. The hub 312 can include a plurality of ports. The hub 312 can include a distal port to which the needle 302 can be attached and placed in fluid communication with the hub. The hub 312 can include one or more proximal ports. The proximal ports can guide a catheter 304 inserted though the hub 312 into the central lumen of the needle 302. The proximal ports can attach the hub 312 to respective fluid lines and place the hub in fluid communication with said fluid lines. The fluid lines can be used to direct fluid into the hub 312 and through a needle 302 attached thereto. The proximal and distal ports of the hub 312 can be Luer type connectors or zero-dead-volume connectors. As shown in FIG. 24B, the hub 312 can include a distal port attached to the needle 302 and a proximal port through which a dual-lumen catheter 304 is inserted to guide the catheter through the needle. The dual lumen catheter 304 can split or bifurcate at a location proximal to the hub 312 into first and second fluid lines, e.g., for carrying a drug and a buffer, respectively. The hub 312 can include one or more additional ports through which a fluid can be introduced into, or withdrawn from, the needle 302. These ports can be used to deliver drug or buffer to the needle 302 or to aspirate fluid from the needle, instead of or in addition to doing so using the catheter 304.

Figure 24C:
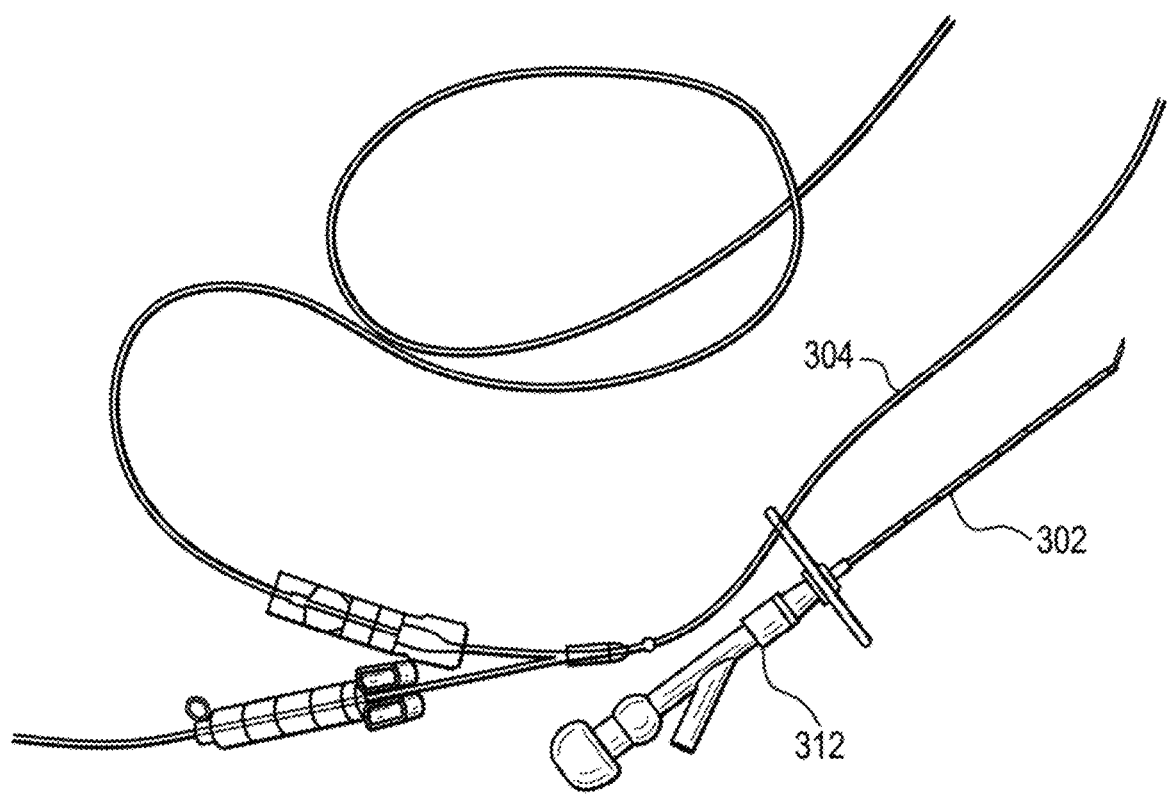
FIG. 24C is a perspective view of a needle, hub, and catheter of the system of FIG. 24A, shown with the catheter outside of the needle.
Figure 24D:
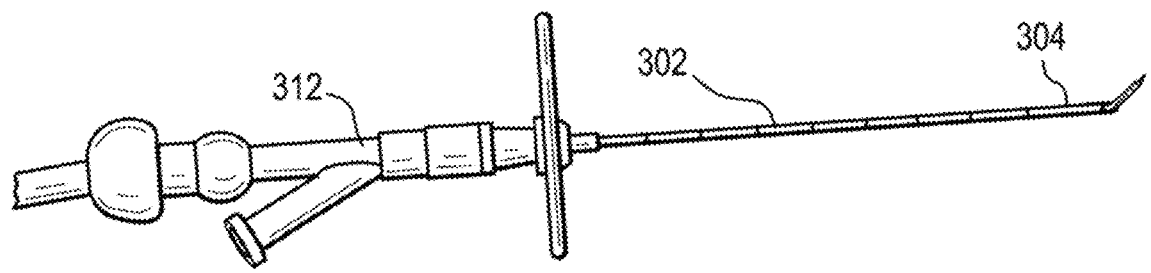
FIG. 24D is a perspective view of a needle, hub, and catheter of the system of FIG. 24A, shown with the catheter inserted through the needle.

As shown in FIGS. 24C-24D, the hub 312 can be a "Y" hub. The hub 312 can include a distal port attached to the needle 302 and a proximal port through which a dual-lumen catheter 304 is inserted to guide the catheter through the needle. The dual lumen catheter 304 can split or bifurcate at a location proximal to the hub 312 into first and second fluid lines, e.g., for carrying a drug and a buffer, respectively. The hub 312 can include one or more additional ports through which a fluid can be introduced into, or withdrawn from, the needle 302. These ports can be used to deliver drug or buffer to the needle 302 or to aspirate fluid from the needle, instead of or in addition to doing so using the catheter 304.

In some embodiments, the hub can be omitted and fluid can be delivered to or aspirated from the needle 302 directly. For example, the needle 302 can be directly attached to the pump system 310 via one or more fluid lines, or a catheter 304 can be directly attached to the pump system via one or more fluid lines and inserted through the needle without a proximal hub.

The system 300 can include one or more valves to control or limit fluid flow through the system. For example, the system 300 can include check valves 314 disposed in-line with respective fluid paths from the pump system 310 to the patient to isolate the paths from one another in a single direction or in both directions. In an exemplary arrangement, the system 300 can include first and second independent fluid sections or channels. The first fluid section or channel can include a first pump configured to deliver a first fluid through a first fluid tube and through a first fluid lumen of the catheter 304. The second fluid section or channel can include a second pump configured to deliver a second fluid through a second fluid tube and through a second fluid lumen of the catheter 304. A first valve, e.g., a check valve, can be disposed in the catheter, in the first fluid tube, or in the first pump to prevent fluid being infused or aspirated by the second pump from entering the first fluid section of the system. Similarly, a second valve, e.g., a check valve, can be disposed in the in the catheter, in the second fluid tube, or in the second pump to prevent fluid being infused or aspirated by the first pump from entering the second fluid section of the system. In some embodiments, only one of the first and second fluid channels includes a valve. The first fluid section can be used to infuse a drug and the second fluid section can be used to infuse a fluid, e.g., drug, buffer, chaser, CSF, artificial CSF, saline, etc. The first fluid section can be used to infuse a fluid and the second fluid section can be used to aspirate a fluid.

The needle 302 or the catheter 304 can include a sensor 314 (e.g., a pressure sensor) mounted adjacent a distal tip of thereof. Accordingly, upon insertion of the needle 302 or catheter 304 into the patient, the sensor 314 can measure the pressure or other properties of the patient's CSF. The needle 302 or catheter 304 can also include an integrated or remote display for displaying the output of the sensor 314 to a user. In some embodiments, the display can be mounted along the length of the needle or catheter, distal to a proximal hub or other connector. The needle body can be a tubular shaft with a sharpened or angled tip. A distal end of the needle can be curved in one or more planes.

Figure 24E:
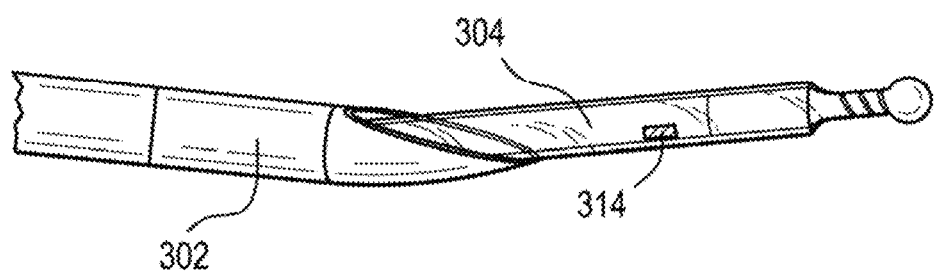
FIG. 24E is a perspective view of a catheter of the system of FIG. 24A protruding from a needle of the system of FIG. 24A.
Figure 24F:
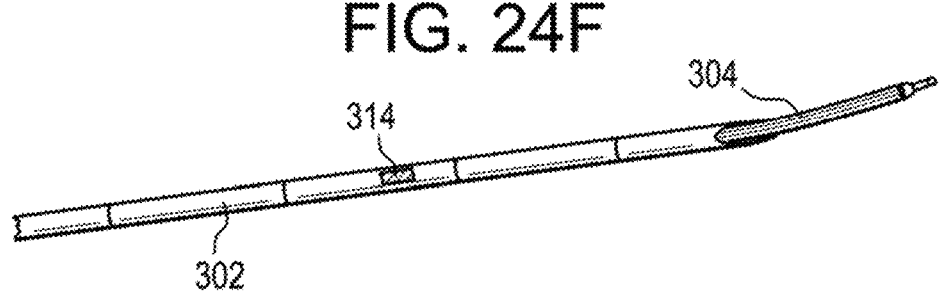
FIG. 24F is a perspective view of a catheter of the system of FIG. 24A protruding from a needle of the system of FIG. 24A.
Figure 24G:
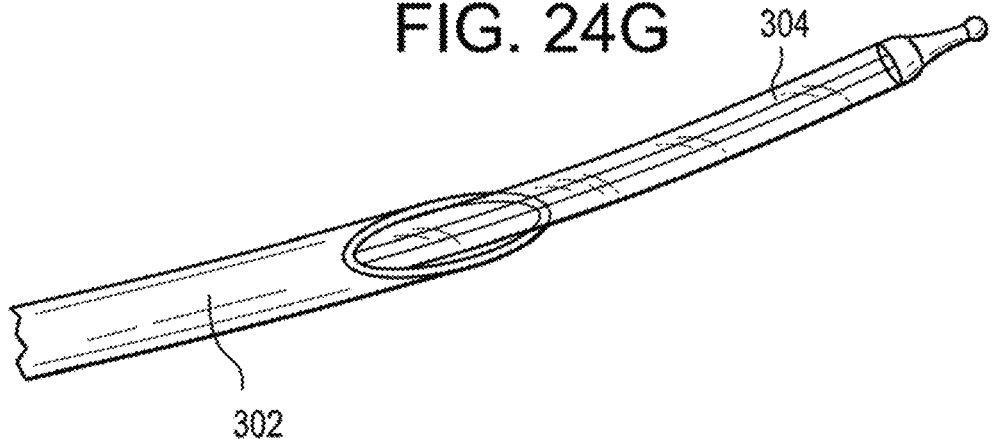
FIG. 24G is a perspective view of a catheter of the system of FIG. 24A protruding from a needle of the system of FIG. 24A.

As shown in FIGS. 24E-24G, the catheter 304 can be inserted through the needle 302 such that a distal end of the catheter protrudes from the needle. Alternatively, the catheter can be inserted such that it is recessed relative to the distal end of the needle, or such that the distal ends of the needle and of the catheter are flush.

The needle 302 can have a length in the range of about 2 inches to about 5 inches, e.g., a length of about 3.5 inches. The hub 312 can have a length in the range of about 1 inch to about 3 inches, e.g., about 2 inches. The needle 302 can have an outside diameter in the range of about 26 gauge to about 10 gauge, e.g., about 17 gauge. The catheter 304 can have an outside diameter in the range of about 0.020 inches to about 0.125 inches. The needle 302 can have an inside diameter in the range of about 0.020 inches to about 0.2 inches. The catheter 304 can be inserted through the needle 302 such that the catheter protrudes from the distal end of the needle by a protrusion distance. The protrusion distance can be in the range of about 1 mm to about 5 cm, e.g., about 1 cm. The protrusion distance can be zero such that the catheter 304 does not protrude from the needle 302. Limiting the degree to which the catheter 304 protrudes from the needle 302 can advantageously obviate the need to thread the catheter through the intrathecal space. This can be make the delivery procedure safer and/or less invasive and reduce the level of skill required to use the system 300.

Figure 25A:
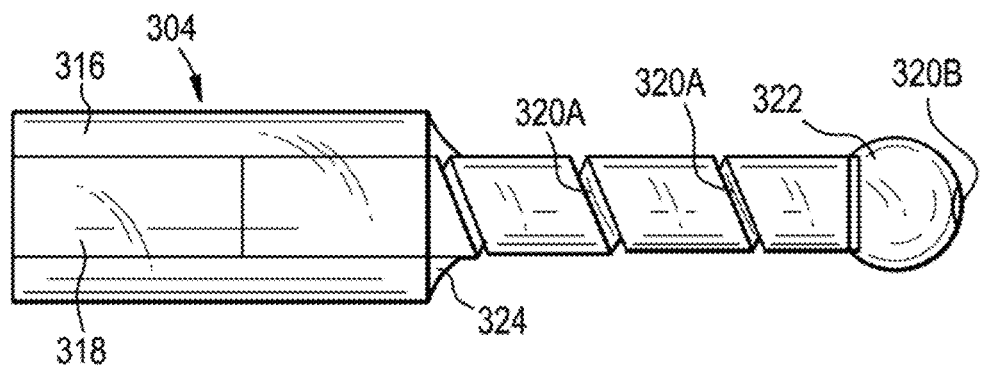
FIG. 25A is a side view of a catheter tip having a helical fluid port.
Figure 25B:
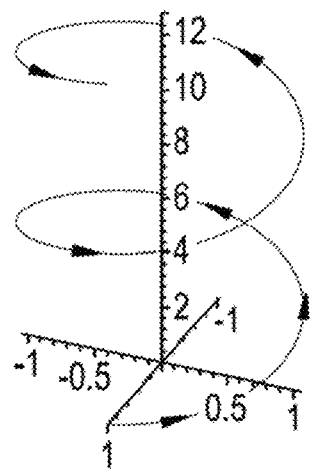
FIG. 25B is a schematic representation of the geometry of the helical port of FIG. 25A.

The catheter 304 can have any of the features of the catheters described above. FIGS. 25A-25D illustrate an exemplary catheter 304 that can be used in the system 300. The catheter 304 can include a tubular body 316 that defines one or more fluid lumens 318. The catheter 304 can include one or more ports 320 that place the inner fluid lumen 318 of the catheter in fluid communication with the exterior of the catheter. Fluid can be infused or aspirated through the ports 320. The illustrated catheter includes a port 320A in the form of a helical-shaped slit. FIG. 25B schematically illustrates an exemplary helical-shaped slit geometry in three-dimensions. The slit 320A can be formed in the sidewall of the catheter, in the sidewall of a reduced-diameter distal portion of the catheter, or in the sidewall of an inner tube projecting from a distal end of the catheter. In embodiments that include an inner tube, the inner tube can extend the full length of the catheter or along only a portion of the catheter length. The inner tube can be affixed to the catheter using an adhesive, sonic welding, or other techniques. Alternatively, the inner tube can be formed integrally with the main catheter body, e.g., via a molding or milling process. The catheter can include a front-facing port 320B. The front-facing port can be defined by a circular opening formed in a distal-facing end wall of the catheter 304.

Figure 25C:
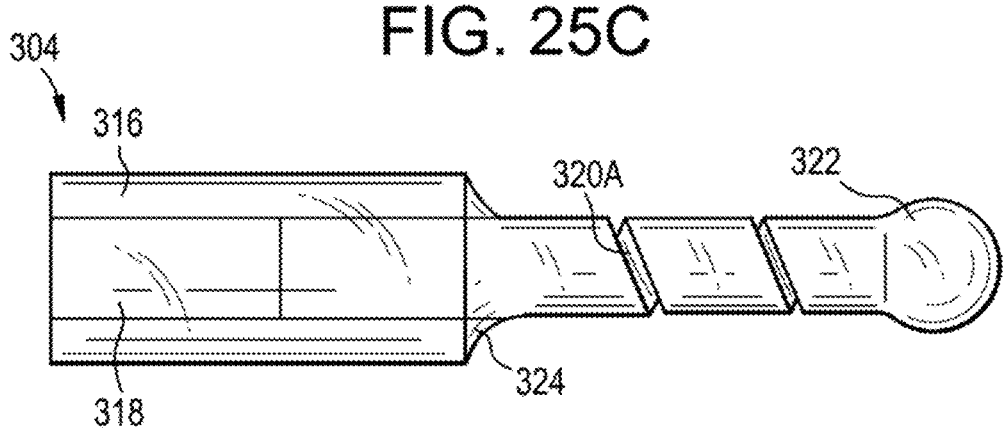
FIG. 25C is a perspective view of the catheter tip of FIG. 25A.
Figure 25D:
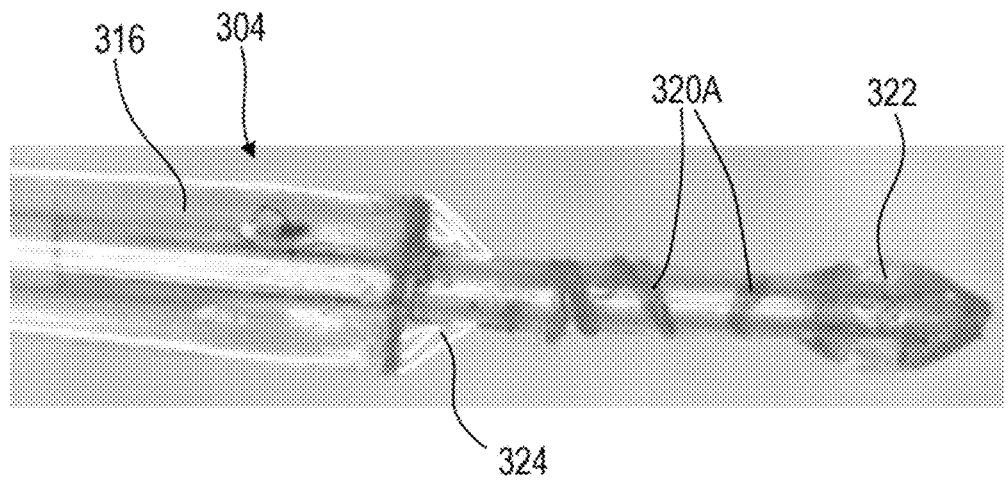
FIG. 25D is another perspective view of the catheter tip of FIG. 25A.
Figure 25E:
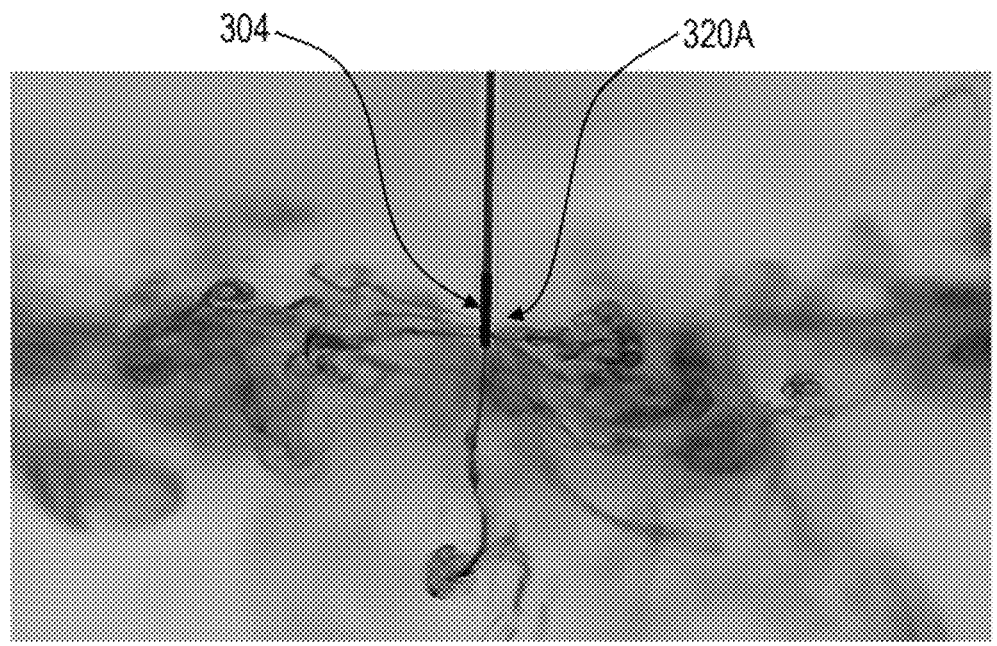
FIG. 25E is a photograph of an exemplary distribution pattern achieved using the catheter tip of FIG. 25A.

While a helical-shaped slit is shown, the catheter 304 can alternatively or additionally have ports with other shapes. Exemplary port shapes include circular holes, a plurality of discrete holes arranged in a helical pattern about the catheter, cage or mesh type openings, and so forth. As shown in FIG. 25E, a helical-shaped slit port 320A can advantageously increase the dispersion of fluid infused through the catheter 304 into a surrounding medium.

The distal end of the catheter 304 can have an atraumatic geometry. For example, the catheter can include a substantially spherical or bulb-shaped portion 322 at a distal end thereof as shown. In embodiments in which the catheter 304 includes a stepped-down or reduced-diameter portion, the catheter can include a fillet or flange 324 to transition between the different diameters. For example, as shown in FIGS. 25C-25D, a tapered transition can be formed between the reduced distal portion of the catheter and the enlarged proximal portion of the catheter. The tapered transition can be conical. The tapered transition can be convexly or concavely curved.

The distal portion of the catheter 304 can be formed from, coated with, or impregnated with a radiopaque, magnetic, or other image-able material. For example, a separate inner tube in which the fluid port is formed can be formed from such a material and attached to the outer catheter body. The image-able material can facilitate visualization and guidance of the tip of the catheter under fluoroscopy or other imaging techniques such as MRI, CT, PET, and the like.

The catheter 304 can be formed form any of a variety of materials. Exemplary materials include polyimide, PEEK, polyurethane, silicone, and combinations thereof.

Figure 26:
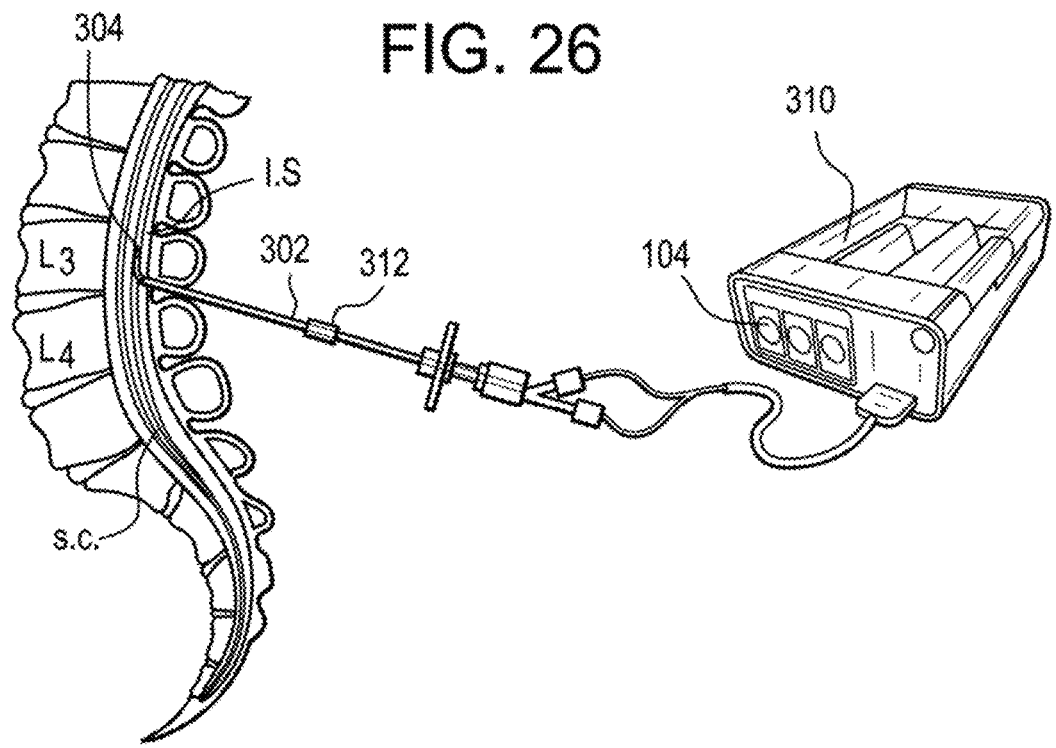
FIG. 26 is a schematic diagram of an exemplary method of using the system of FIG. 24A with a patient.

The drug delivery system 300 can be used in a manner similar or identical to the drug delivery systems described above. FIG. 26 illustrates an exemplary method of using the system 300. As shown, the needle 302 can be inserted percutaneously into a patient in the lumbar region of the patient's spine, e.g., using standard lumbar puncture technique. The curved distal end of the needle 302 can help guide the distal opening of the needle into the intrathecal space IS without damaging the spinal cord SC. The needle 302 can be inserted into the intrathecal space only to a small degree, e.g., about 1 cm in to the intrathecal space. A catheter 304 can be inserted through the needle 302 to position a distal tip of the catheter within the intrathecal space. As noted above, in some embodiments, the catheter 304 only protrudes from the needle 302 by a small amount, e.g., by about 1 cm. The proximal end of the catheter 304 or the needle 302 can be coupled to a pump system 310 for infusing or aspirating fluid through the catheter or the needle. In some arrangements, the pump system includes separate drug and buffer channels, each having a respective pump. The pump system can be coupled to dual lumens of the catheter, e.g., at a bifurcated proximal portion of the catheter. In other arrangements, a first channel of the pump system can be coupled to the needle and a second channel of the pump system can be coupled to the catheter. In other arrangements, the catheter can be omitted and the pump system can include a single channel coupled to the needle, or can include multiple channels coupled to the needle.

A controller 104, e.g., a programmable computer processor, or a user can control the pump system 310 to infuse and/or aspirate fluid from the patient via the catheter and/or needle.

In an exemplary embodiment, a drug can be infused through a first fluid channel of the system 300 and, thereafter, a chaser can be infused through the same or a different fluid channel of the system to push the drug through the intrathecal space of the patient. Exemplary chasers include drug-containing fluid, buffer fluid, artificial CSF, natural CSF previously aspirated from the patient, saline, etc. In some embodiments, the chaser can be CSF previously aspirated from the patient and the CSF can be aspirated and infused using the same syringe without removing the CSF from the syringe, thereby maintaining a closed sterile system.

The catheter 304 or needle 302 can include any of the features of the needle 402 described below.

Figure 28A:
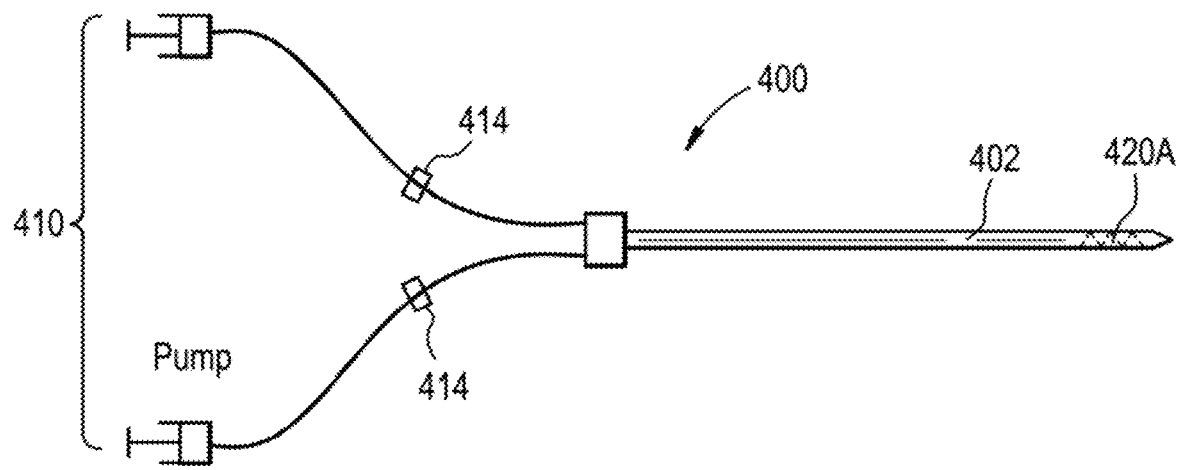
FIG. 28A is a schematic view of a drug delivery system.

FIG. 28A illustrates an exemplary drug delivery system 400 that can be used for intrathecal infusion and/or aspiration of fluid. The system 400 is substantially similar to the system 300 described above, though in the system 400, fluid is delivered or aspirated directly through the needle 402, without inserting a catheter through the needle. The needle 402 can be coupled at a proximal end thereof to a pump system 410. As in the systems described above, the pump system 410 can have multiple fluid channels (e.g., one channel for drug and another channel for chaser). The pump system 410 can be connected to the needle 402 by one or more fluid tubes. A hub can be formed on or coupled to the needle 402 to connect the needle to the fluid tubes. For example, a Y-connector port can be used to connect the pump system 410 to the needle 402. The needle 402 can have various diameters and, in an exemplary embodiment, can be a 22 gauge needle. One or more valves 414 can be disposed in-line in the fluid tubes, in the needle 402, or in the pump system 410. The valves 414 can be one-way valves, check valves, etc.

Figure 28B:
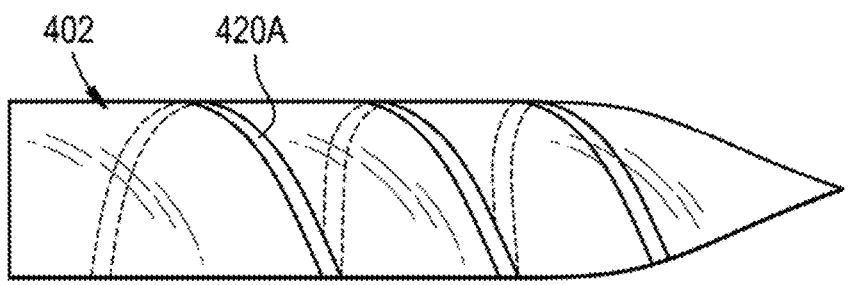
FIG. 28B is a side view of a tip of a needle of the system of FIG. 28A.
Figure 29:
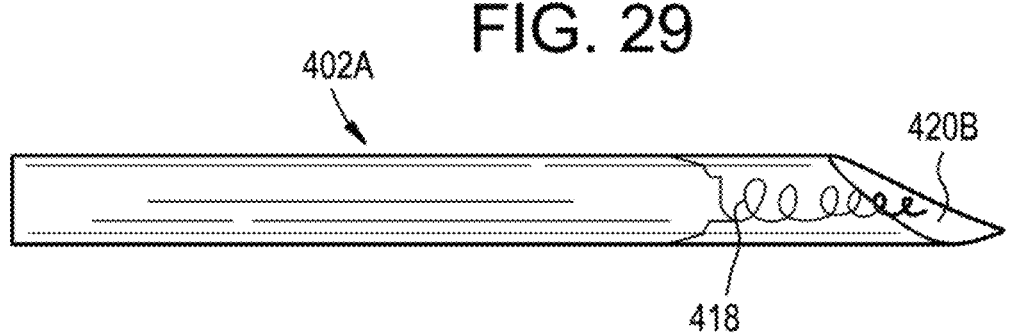
FIG. 29 is a sectional side view of a tip of another needle that can be used with the system of FIG. 28A.
Figure 30A:
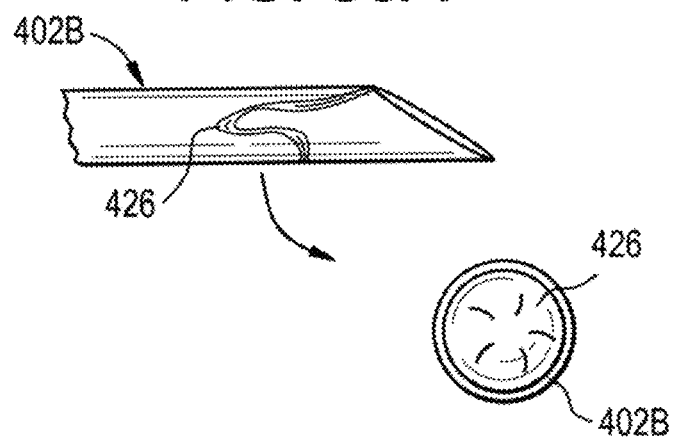
FIG. 30A is a schematic view of a tip of another needle that can be used with the system of FIG. 28A.
Figure 30B:
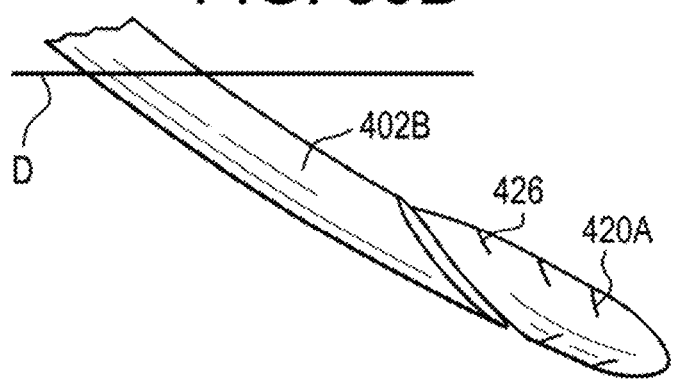
FIG. 30B is a schematic view of the needle tip of FIG. 30A with an inflatable member deployed therefrom.
Figure 30C:
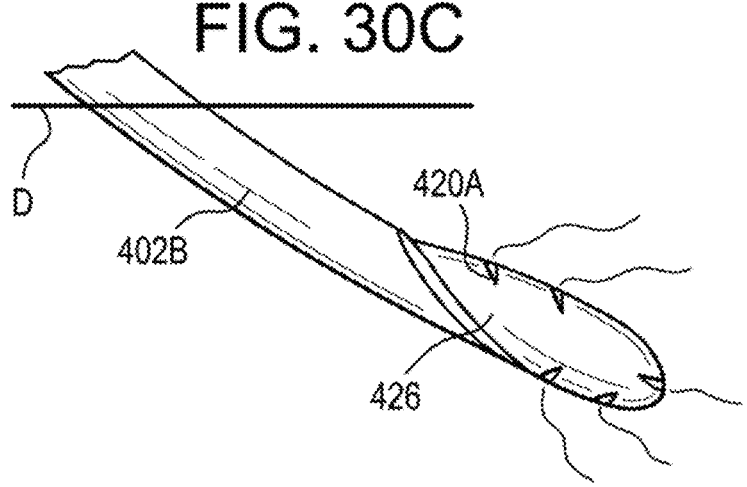
FIG. 30C is a schematic view of the needle tip of FIG. 30A with a fluid being infused through the inflatable member.

The needle can have any of a variety of fluid ports formed therein. For example, as shown in FIGS. 28A-28B, the needle 402 can include a helical slit fluid port 420A formed adjacent a distal tip of the needle. The fluid port 420A can be laser-cut. As another example, as shown in FIG. 29, the needle 402A can have a helical inner lumen 418 disposed adjacent to a distal fluid port 420B. The helically-shaped inner lumen 418 can facilitate turbulent flow of infusate through the distal fluid port to better disperse the fluid. The helically-shaped inner lumen 418 can be a tubular passage that defines a plurality of looped coils. The needle 402 can include a sharpened pencil tip. As another example, as shown in FIGS. 30A-30C, the needle 402B can include an inflatable member 426, e.g., a balloon or membrane, disposed in a distal end of the needle. The needle 402 can include a sharpened tip. The inflatable member 426 can be initially retracted within the tip of the needle 402, and the sharpened tip can be used to pierce the patient's dura D or other tissue to facilitate needle insertion. Once the distal tip of the needle 402 is positioned in a desired location, e.g., within the intrathecal space, the inflatable member 426 can be deployed outside of the needle, as shown in FIG. 30B. Deployment of the inflatable member 426 can be achieved by infusing fluid through the needle 402. The inflatable member 426 can include one or more fluid ports formed therein, through which fluid can be infused or aspirated. For example, as shown in FIG. 30C, the inflatable member 426 can include a helical fluid port 420A formed therein through which fluid can be infused. The inflatable member 426 can be formed from a soft material, e.g., a material softer than the material used to form the needle 402, to define an atraumatic tip when the inflatable member is deployed. The inflatable member 426 can be formed from a flexible biocompatible material such as silicone.

The needle 402 can include any of the features of the catheter 304 or needle 302 described above.

In some embodiments, volume displacement of CSF can be used to move an infused drug through the intrathecal space of the patient. For example, fluid can be aspirated from the intrathecal space before, during, or after drug infusion to urge the drug in a desired direction within the intrathecal space. The fluid used for such volume displacement can be in the range of about 1% to about 20% of the patient's total CSF volume. The fluid can be aspirated from the patient and then subsequently re-infused.

The systems disclosed herein can be used for patient-specific infusion. In an exemplary patient-specific infusion method, a specific patient's CSF volume can be determined, for example by calculating or estimating. For example, a preoperative or intraoperative image of the patient can be captured. The image can be one or more MRI images of the patient's head and spine and/or entire central nervous system. Image processing routines or manual estimation techniques can be used, e.g., with correlation to a 3D anatomical model, to calculate or estimate the total CSF volume of the patient. The calculated or estimated CSF volume can be used to tailor an infusion and/or aspiration profile to that particular patient. For example, about 1% to about 20% of the calculated or estimated total CSF volume can be aspirated from the patient and re-infused behind an infused drug to urge the drug in a desired direction, e.g., cranially or caudally within the patient's intrathecal space.

In some embodiments, a method can include measuring the CSF head to body volume of a human using magnetic resonance imaging or other means. The method can include therapy or drug infusion performed by removal and/or infusion of 0.5 to 20% of the patient's total CSF volume. The method can include therapy or drug infusion performed by removal and/or infusion of artificial CSF, buffer solutions, or saline in conjunction with delivery of drug or therapy. The method can include delivering the drug or therapy at volume flow rates in the range of about 0.1 ml/min to about 30 ml/min. The drug and additional volume (e.g., aspirated CSF, artificial CSF, buffer, etc.) can be infused using pulsatile delivery as disclosed herein and/or using pulsatile delivery based on a physiological parameter as disclosed herein. The drug and additional volume can be infused serially or in parallel. Volume displacement and/or patient-specific drug or therapy infusion can advantageously provide better biodistribution of the infused drug.

Figure 27:
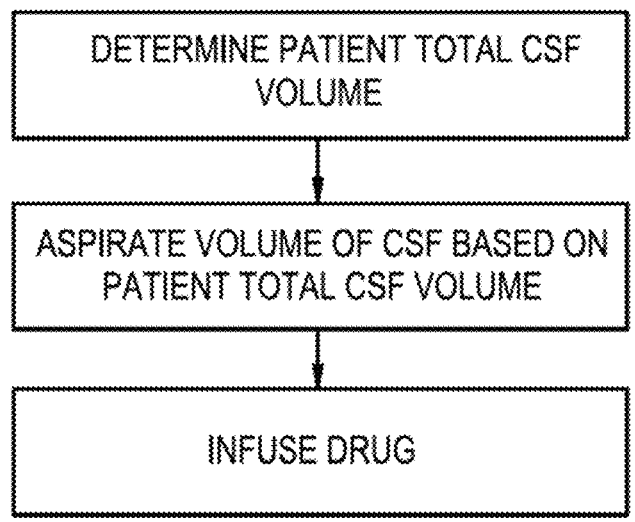
FIG. 27 is a schematic diagram of an exemplary method of patient-specific infusion.

FIG. 27 illustrates an exemplary method of patient-specific infusion. As shown, the method can include determining the patient's total CSF volume, aspirating a volume of CSF based on the patient's total CSF volume, and infusing a drug.

The infusion flow rate of the systems disclosed herein can be in the range of about 0.001 ml/min to about 50 ml/min.

U.S. Provisional Application No. 62/159,552 filed on May 11, 2015, U.S. Provisional Application No. 62/239,875 filed on Oct. 10, 2015, U.S. Provisional Application No. 62/303,403 filed on Mar. 4, 2016, and U.S. application Ser. No. 15/151,585 filed on May 11, 2016 are hereby incorporated herein by reference in their entirety.

Although the invention has been described by reference to specific embodiments, it should be understood that numerous changes may be made within the spirit and scope of the inventive concepts described. Accordingly, it is intended that the invention not be limited to the described embodiments.

What is claimed is:

1. A drug delivery device, comprising:
   an elongate body having a fluid lumen formed therein; and
   a fluid port formed in the drug delivery device, the fluid port being defined by a helical slit formed in a wall of the drug delivery device;
   wherein the helical slit extends from an interior surface of the wall to an exterior surface of the wall of the delivery device to thereby radially deliver fluid to an exterior of the drug delivery device.

2. The drug delivery device of claim 1, wherein the helical slit extends from an interior surface of the body to an exterior surface of the body.

3. The drug delivery device of claim 1, wherein the helical slit acts as a fluid communication path between an interior of the fluid lumen and an exterior of the drug delivery device.

4. The drug delivery device of claim 1, wherein the helical slit is formed through an exterior wall of the drug delivery device.

5. The drug delivery device of claim 1, wherein the helical slit is formed in a sidewall of a reduced-diameter portion of the drug delivery device.

6. The drug delivery device of claim 1, wherein the helical slit is formed in a sidewall of an inner tube that extends within and projects forwardly from a distal end of the body.

7. The drug delivery device of claim 1, further comprising an atraumatic distal tip defined by a substantially spherical bulb.

8. The drug delivery device of claim 1, further comprising a second, distal-facing fluid port.

9. The drug delivery device of claim 1, further comprising a tapered transition between a larger diameter proximal portion of the drug delivery device and a reduced diameter distal portion of the drug delivery device.

10. The drug delivery device of claim 9, wherein the tapered transition is at least one of conical, convex, and concave.

11. The drug delivery device of claim 1, wherein the drug delivery device comprises a catheter.

12. The drug delivery device of claim 1, wherein the drug delivery device comprises a needle.

13. The drug delivery device of claim 1, further comprising an inflatable member disposed at a distal end of the drug delivery device.

14. The drug delivery device of claim 13, wherein the inflatable member is deployable from within a sharpened distal tip of the drug delivery device.

15. The drug delivery device of claim 13, wherein the inflatable member includes a fluid port therein.

16. The drug delivery device of claim 15, wherein the fluid port of the inflatable member comprises the helical slit.

17. A drug delivery device, comprising:
   an elongate body having a fluid lumen therein and a fluid port through which fluid can move between an interior of the fluid lumen and a location exterior to the drug delivery device;
   wherein at least a portion of the fluid lumen is helically-shaped, the helically-shaped portion of the fluid lumen being adjacent to the fluid port and configured to facilitate turbulent flow of fluid through the fluid port.

18. The drug delivery device of claim 17, wherein the helically-shaped portion of the fluid lumen comprises a tubular passage that defines a plurality of looped coils.

19. A drug delivery device, comprising:
   a needle having a sharpened distal tip; and
   an inflatable member selectively deployable from a distal end of the sharpened tip, the inflatable member having a fluid port formed therein;
   wherein the fluid port comprises a helical slit.

* * * * *